United States Patent
Vortman et al.

(10) Patent No.: US 11,684,807 B2
(45) Date of Patent: Jun. 27, 2023

(54) OPTIMIZATION OF TRANSDUCER CONFIGURATIONS IN ULTRASOUND PROCEDURES

(71) Applicants: Kobi Vortman, Haifa (IL); Yoav Levy, Hinanit (IL); Shahar Rinott, Haifa (IL)

(72) Inventors: Kobi Vortman, Haifa (IL); Yoav Levy, Hinanit (IL); Shahar Rinott, Haifa (IL)

(73) Assignee: Insightec Ltd., Tirat Carmel (IL)

( * ) Notice: Subject to any disclaimer, the term of this patent is extended or adjusted under 35 U.S.C. 154(b) by 872 days.

(21) Appl. No.: 16/233,744

(22) Filed: Dec. 27, 2018

(65) Prior Publication Data
US 2020/0205782 A1 Jul. 2, 2020

(51) Int. Cl.
*A61N 7/00* (2006.01)
*A61N 7/02* (2006.01)
(Continued)

(52) U.S. Cl.
CPC ............... *A61N 7/02* (2013.01); *A61B 5/015* (2013.01); *G06N 20/20* (2019.01);
(Continued)

(58) Field of Classification Search
CPC ....... A61B 8/4494; A61B 5/015; A61B 8/469; A61B 8/5207; G06N 20/20
See application file for complete search history.

(56) References Cited

U.S. PATENT DOCUMENTS

| 9,119,955 B2 | 9/2015 | Zur et al. | |
| 2004/0049110 A1* | 3/2004 | Cai | B06B 1/0629 600/437 |

(Continued)

FOREIGN PATENT DOCUMENTS

| EP | 3417911 A1 | 12/2018 |
| WO | 200180708 A2 | 11/2001 |

(Continued)

OTHER PUBLICATIONS

Sassaroli et al., "Resonance frequency of microbubbles in small blood vessels: a numerical study", 2005, Physics in Medicine & Biology, 50, 5293-5305 (Year: 2005).*

(Continued)

*Primary Examiner* — Keith M Raymond
*Assistant Examiner* — Adam D. Kolkin
(74) *Attorney, Agent, or Firm* — Morgan, Lewis & Bockius LLP

(57) ABSTRACT

Various approaches to delivering ultrasound energy to a target region include an ultrasound transducer having multiple transducer elements for generating a focal zone of acoustic energy at the target region, wherein one or more transducer elements are partitioned into multiple contiguous sub-regions having a common directionality; one or more driver circuits connected to the transducer element(s); a switch matrix having multiple switches for switchably connecting the sub-regions to the driver circuit(s), each of the sub-regions being associated with one of the switches; and a controller configured to (i) determine an optimal sonication frequency for maximizing a peak acoustic intensity in the focal zone; and (ii) based at least in part on the determined optimal sonication frequency, activate one or more switches in the switch matrix for causing the corresponding sub-region(s) to transmit ultrasound pulses to the target region.

24 Claims, 16 Drawing Sheets

(51) Int. Cl.
  *G06N 20/20* (2019.01)
  *A61B 5/01* (2006.01)
(52) U.S. Cl.
  CPC .............. *A61N 2007/0073* (2013.01); *A61N 2007/0078* (2013.01); *A61N 2007/0086* (2013.01); *A61N 2007/0095* (2013.01)

(56) References Cited

U.S. PATENT DOCUMENTS

| | | | | |
|---|---|---|---|---|
| 2004/0236253 | A1* | 11/2004 | Vortman | G10K 11/346 601/2 |
| 2010/0041989 | A1* | 2/2010 | Sehgal | A61B 8/0833 601/2 |
| 2012/0209150 | A1* | 8/2012 | Zeng | A61N 7/02 601/2 |
| 2014/0026665 | A1* | 1/2014 | Keady | A61B 5/14532 73/587 |
| 2014/0276075 | A1* | 9/2014 | Blalock | A61B 8/4483 600/459 |
| 2015/0265857 | A1 | 9/2015 | Barnes et al. | |
| 2015/0374287 | A1* | 12/2015 | Vahala | A61N 7/02 600/411 |
| 2016/0007960 | A1* | 1/2016 | Son | A61B 8/5207 601/3 |
| 2016/0364862 | A1* | 12/2016 | Reicher | G16H 50/50 |
| 2018/0193675 | A1 | 7/2018 | Vortman et al. | |

FOREIGN PATENT DOCUMENTS

| | | | |
|---|---|---|---|
| WO | 200243805 A1 | 6/2002 | |
| WO | WO-2011156624 A2 * | 12/2011 | .......... A61B 8/4438 |
| WO | WO-2013032946 A1 * | 3/2013 | .......... A61B 8/4488 |
| WO | 2014057388 A1 | 4/2014 | |
| WO | 2014135987 A2 | 9/2014 | |
| WO | WO-2014135987 A2 * | 9/2014 | ............... A61N 7/00 |
| WO | WO-2018011631 A2 * | 1/2018 | .......... A61B 6/5217 |

OTHER PUBLICATIONS

Filipowska et al., "Magnetic Resonance-Guided High-Intensity Focused Ultrasound (MR-HIFU) in Treatment of Symptomatic Uterine Myomas", 2014, Polish Journal of Radiology, 79, 439-443 (Year: 2014).*

King Yuk Chan et al: "Monolithic crossbar MEMS switch matrix", IEEE—MTTS International Microwave Symposium. Digest, Jun. 1, 2008 (Jun. 1, 2008), pp. 129-132.

International Search Report and the Written Opinion for International Application No. PCT/IB2019/001238, dated Apr. 3, 2020, 25 pages.

Office Action for corresponding Chinese Patent Application No. 201980086669.8 dated Mar. 8, 2023, 13 pages.

* cited by examiner

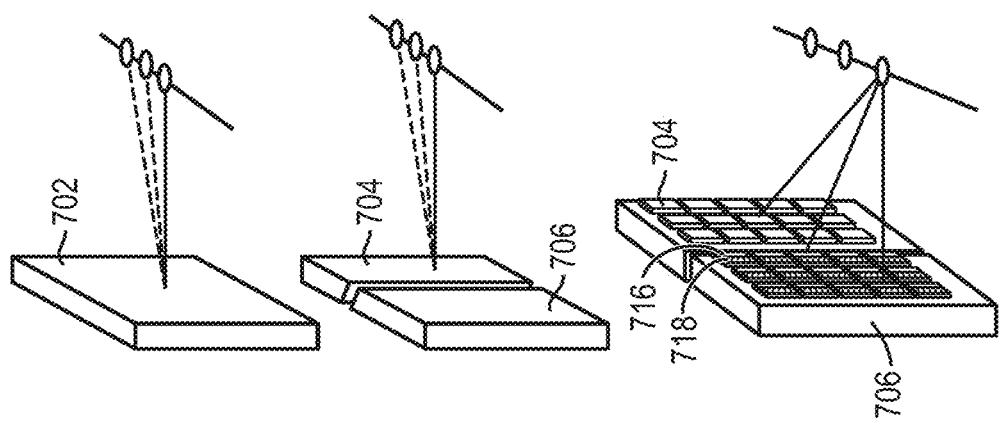
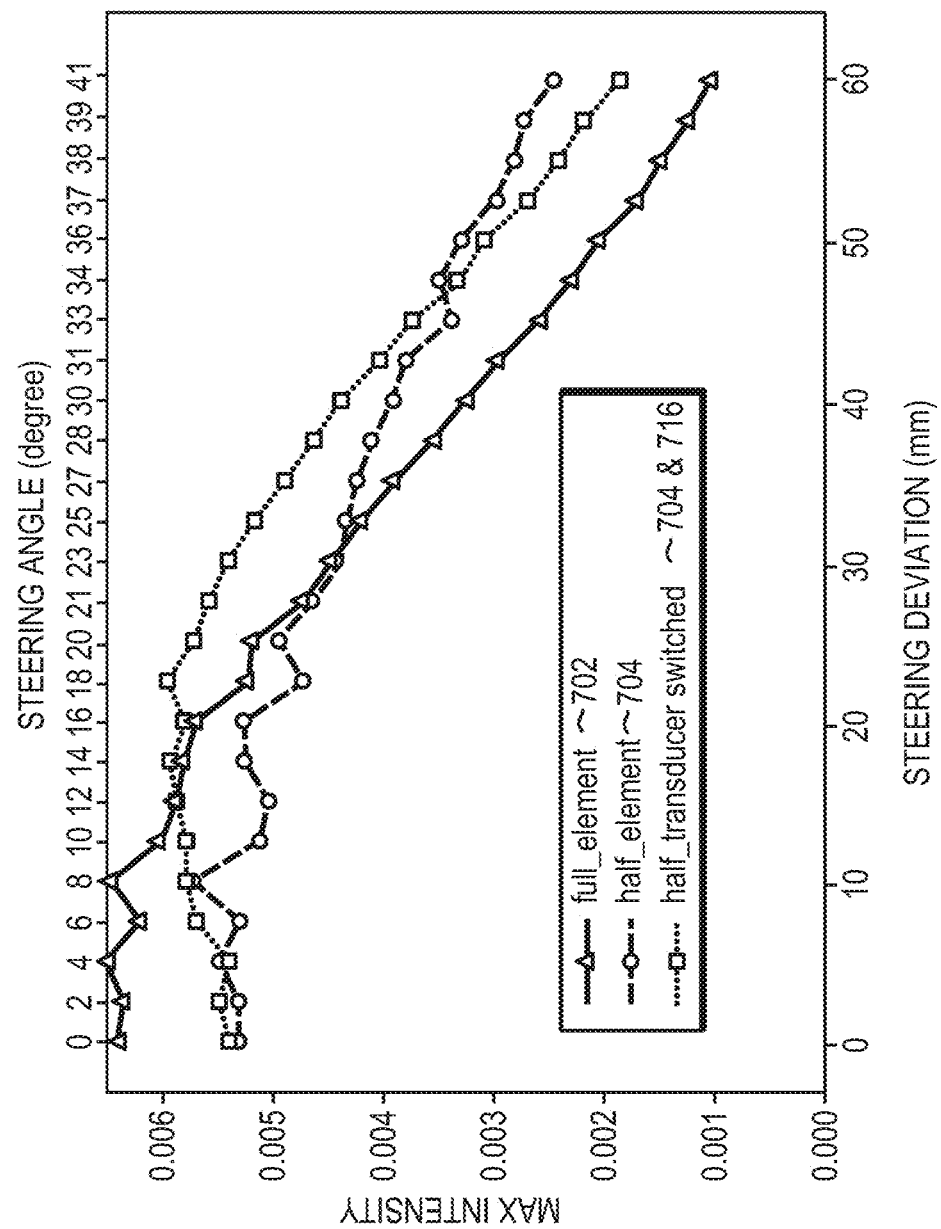
FIG. 7E

OPTIMIZATION OF TRANSDUCER CONFIGURATIONS IN ULTRASOUND PROCEDURES

TECHNICAL FIELD

The present invention relates, generally, to focused-ultrasound procedures, and more particularly to systems and methods for optimizing ultrasound transducer configurations for increased energy deposition at the target.

BACKGROUND

Focused ultrasound (i.e., acoustic waves having a frequency greater than about 20 kilohertz) can be used to image or therapeutically treat internal body tissues within a patient. For example, ultrasonic waves may be used to ablate tumors, eliminating the need for the patient to undergo surgery. For this purpose, a piezo-ceramic transducer is placed external to the patient, but in close proximity to the tissue to be ablated (the "target"). The transducer converts an electronic drive signal into mechanical vibrations, resulting in the emission of acoustic waves (a process hereinafter referred to as "sonication"). The transducer may be shaped so that the waves converge in a focal zone. Alternatively or additionally, the transducer may be formed of a plurality of individually driven transducer elements whose phases (and, optionally, amplitudes) can each be controlled independently from one another and, thus, can be set so as to result in constructive interference of the individual acoustic waves in the focal zone. Such a "phased-array" transducer facilitates steering the focal zone to different locations by adjusting the relative phases between the transducer elements. Magnetic resonance imaging (MRI) may be utilized to visualize the focus and target in order to guide the ultrasound beam.

FIG. 1 illustrates an exemplary focused-ultrasound system 100. The system 100 includes a transducer array 101 having multiple ultrasound transducer elements 102, which are arranged in an array at the surface of a housing 104. The array 101 may comprise a single row or a matrix, or generally any arrangement, of transducer elements 102. The array 101 may have a curved (e.g., spherical or parabolic) shape, as illustrated, or may include one or more planar or otherwise shaped sections. Its dimensions may vary, depending on the application, between millimeters and tens of centimeters. The transducer elements 102 may be piezoelectric ceramic elements, or be made of piezo-composite materials or any other materials capable of converting electrical energy to acoustic energy. To damp the mechanical coupling between the elements 102, they may be mounted on the housing 104 using silicone rubber or any other suitable damping material or laterally separated mechanically (e.g., air spacing).

The transducer elements 102 are driven via separate drive channels by a controller 106. For n transducer elements 102, the controller 106 may contain n control circuits each comprising an amplifier and a phase control circuit, with each control circuit driving one of the transducer elements 102. The controller 106 may split a radio-frequency (RF) input signal, typically in the range of 0.1 MHz to 10 MHz, into n channels for the n control circuits. In conventional systems, the controller 106 is configured to drive the individual transducer elements 102 of the array at the same frequency, but at different phases and different amplitudes so that they collectively produce a focused ultrasound beam at a desired location. The controller 106 desirably provides computational functionality, which may be implemented in software, hardware, firmware, hardwiring, or any combination thereof, to compute the required phases and amplitudes for a desired focus location; these phase/amplitude computations may include corrections that compensate for aberrations resulting from ultrasound reflection or refraction at tissue interfaces or propagation in tissue having various acoustic parameters, which may be determined based, e.g., on computer tomography (CT) and/or MRI or other images of the anatomical region of interest. In general, the controller 106 may include several separable apparatus, such as a frequency generator, a beamformer containing the amplifier and phase control circuitry, and a computer (e.g., a general-purpose computer) performing the computations and communicating the phases and amplitudes for the individual transducer elements 102 to the beamformer. Such systems are readily available or can be implemented without undue experimentation.

The system 100 may further include an MRI apparatus 108 in communication with the controller 106 for performing MRI-guided focused ultrasound treatment. An exemplary apparatus 108 is illustrated in more detail in FIG. 2. The apparatus 108 may include a cylindrical electromagnet 204, which generates a static magnetic field within a bore 206 of the electromagnet 204. During medical procedures, a patient is placed inside the bore 206 on a movable support table 208. A region of interest 210 within the patient (for example, the patient's head) may be positioned within an imaging region 212 wherein the magnetic field is substantially homogeneous. An RF transmitter coil 214 surrounding the imaging region 212 emits RF pulses into the imaging region 212, and receives MR response signals emitted from the region of interest 210. The MR response signals are amplified, conditioned, and digitized into raw data using an image-processing system 216, and further transformed into arrays of image data by methods known to those of ordinary skill in the art. Based on the image data, a treatment region (e.g., a tumor) is identified. The ultrasound phased array 220, disposed within the bore 206 of the MRI apparatus and, in some embodiments, within the imaging region 212, is then driven so as to focus ultrasound into the treatment region. The MRI apparatus 108 facilitates visualizing the focus 112 based on an effect it has on the sonicated tissue. For example, any of a variety of MRI-based thermometry methods may be employed to observe the temperature increase resulting from ultrasound absorption in the focus region. Alternatively, MR-based acoustic radiation force imaging (ARFI) may be used to measure the tissue displacement in the focus. Such measurements of the focus can serve as feedback for driving the ultrasound transducer array 220 so as to maximize the peak intensity.

The goal of focused-ultrasound treatment is generally to effectively deposit a maximal acoustic energy at the target while minimizing the exposure of healthy tissue surrounding the target, as well as tissues along the path between the transducer and the target, to ultrasound. The deposited acoustic energy generally correlates to the peak intensity or acoustic power of the focused beam and may cause heating and/or vibration of the target tissue. For example, heat $Q$ resulting from the acoustic energy at a point (x, y, z) in the tissue is given by:

$$Q(x,y,z)=2\alpha \cdot f \cdot I(x,y,z),$$

where f represents the frequency of the ultrasound waves/pulses (measured in MHz); $\alpha$ represents the absorption coefficient of the tissue at that frequency (measured in $cm^{-1} \cdot MHz^{-1}$); and I(x, y, z) represents the ultrasound intensity at the point (x, y, z). The temperature increase at the point (x, y, z) resulting from the heat can then be computed using a bioheat transfer equation:

$$\frac{\partial T(x, y, z)}{\partial t} = \frac{\kappa}{\rho \cdot C} \nabla^2 T(x, y, z) + \frac{Q(x, y, z)}{\rho \cdot C} - \frac{w_b \cdot C_b}{\rho \cdot C}(T(x, y, z) - T_0)$$

where T(x, y, z) represents the temperature at the point (x, y, z) resulting from the heat $Q$; $T_0$ represents the body baseline temperature prior to deposition of the heat $Q$;

$$\frac{\partial T}{\partial t}$$

represents the time derivative of the temperature T; ρ, C, and k represent the density, heat capacity, and thermal conductivity of the tissue, respectively; $W_b$ represents the blood perfusion rate; and $C_b$ represents the specific heat of blood. Accordingly, treatment effects (e.g., the temperature increase) of the ultrasound procedure may be optimized by maximizing the peak acoustic intensity or power of the focused ultrasound beam at the target.

The peak intensity of the focused ultrasound beam, however, may depend on the configurations of the transducer. For example, while the peak intensity at the focal zone may be improved by increasing the ultrasound transmitting frequency, there is a trade-off: a higher fraction of the acoustic energy will also be absorbed on the way to, and therefore never reach, the target region. While some conventional ultrasound treatment procedures have attempted to optimize the ultrasound frequency by taking this trade-off into account, these approaches may not be sufficient to improve the peak intensity at the target region. This is because adjusting the ultrasound frequency based on one parameter (e.g., tissue absorption) may result in changes in other parameters (e.g., the steering angle of the focused beam) that may affect the peak acoustic intensity; indeed, the effects of these parameters on the peak intensity can be substantial. For example, varying the ultrasound frequency may cause the directivity factor of the transducer elements to change, which in turn results in a change in the peak intensity. Accordingly, attempting to increase the peak intensity by basing the selection of the ultrasound frequency on a particular parameter may be self-defeating due to a negative impact on another parameter.

Another parameter that may affect the peak intensity/power in the focal zone involves the physical configurations of the transducer elements. In the conventional ultrasound system 100, the transducer elements 102 in the array 101 are generally "tiled" to form a flat or curved surface; but once manufactured, the configuration (e.g., shape and size) of individual transducer elements 102 cannot be changed. Because the steering ability of the acoustic beam may depend on the size and the number of the transducer elements 102 in the transducer array 101 and the peak intensity of the focused beam may depend on the steering angle, the fixed, non-adjustable configuration of the elements 102 may limit the steering ability, and, as a result, the peak intensity of the focused beam.

Accordingly, there is a need for an approach that simultaneously takes into account multiple parameters relating to the peak intensity of the focused ultrasound beam so as to deliver a net improvement of peak intensity at the target, and which alternatively or in addition enables adjustment of the configuration of the individual ultrasound transducer elements.

SUMMARY

The present invention relates to focused-ultrasound treatment approaches that involve determining an optimal frequency—i.e., one that maximizes the peak acoustic intensity or acoustic power at the target—within a certain frequency range, as well as systems for implementing such approaches. As used herein, the terms "optimal," "optimizing," "maximum," "maximizing", etc. generally involve a substantial improvement (e.g., by more than 10%, more than 20%, or more than 30%) over the prior art, but do not necessarily imply achievement of the best theoretically possible frequency, energy absorption, etc. Rather, optimizing the frequency, or maximizing the acoustic intensity/power at the target, involves selecting the best frequency practically discernible within the limitations of the utilized technology and method. The invention is based on the recognition that the acoustic intensity/power of the focus at the target site is greatly affected by multiple frequency-dependent parameters (such as energy absorption of the acoustic beam at the target tissue and non-target tissue located in the beam path zone, the steering angle, and the focal area of the focus, etc.), and can be significantly improved by selecting an ultrasound frequency that deviates from the conventionally calculated frequency based on one parameter (e.g., energy absorption of the target tissue) only.

In various embodiments, a computational physical model is implemented to simulate the effects of these frequency-dependent parameters on the peak acoustic intensity/power in the focal zone. For example, the treatment effects of each parameter resulting from a change in the sonication frequency may be sequentially evaluated and a "sub-optimal" frequency associated with each parameter may be determined. Subsequently, the optimal frequency for treatment may be determined based at least in part on some or all of the sub-optimal frequencies. (As used herein, the term "sub-optimal" refers to a smaller improvement (e.g., by no more than 10%, no more than 20%, or no more than 30%) over the prior art compared with the improvement produced by applying the optimal frequency.) For example, the sub-optimal frequency associated with each parameter may be assigned a weighting factor corresponding to its relative contribution toward achieving the maximal peak intensity/power; the optimal frequency can then be computed as the weighted sum of the sub-optimal frequencies. Alternatively, the treatment effects of these parameters may be considered simultaneously and the optimal frequency selected so as to maximize the peak intensity/power.

In some embodiments, one evaluated parameter is energy absorption of the acoustic energy at the target and/or non-target region. The physical model may computationally simulate the interactions of the ultrasound beam with the patient's target tissue and/or intervening tissue located between the transducer and target at various frequencies, using, for example, conventional finite-element analysis. In addition, the simulation may be based on a detailed tissue model as acquired by an imaging apparatus (e.g., computer tomography, ultrashort echo-time (TE), MRI, etc.); the model generally includes multiple tissue types or layers (e.g., for ultrasound focusing into the skull, layers of cortical bone, bone marrow, and soft brain tissue) and characterizes their respective anatomic and/or material properties. Based on the simulation results, the first sub-optimal frequency associated with maximal energy absorption at the target is selected.

Another parameter that may be evaluated is the steering angle of the focused beam. Because the focal zone should coincide with the target region, in various embodiments, the steering angle of the focal zone at the target is computed based on the spatial arrangement (e.g., position and orientation) of the transducer with respect to the target. The spatial arrangement may be determined based on images acquired using the imaging apparatus. The physical model may simulate effects on the peak acoustic intensity/power of the focal zone resulting from a change in frequency at the specific steering angle. Based on the simulation, the second sub-optimal frequency associated with the maximal peak intensity/power at the steering angle is selected. In some embodiments, the treatment effects resulting from other parameters, such as the temperatures of the target and non-target regions during treatment, the resonance frequency of microbubbles, etc. may also be simulated and associated sub-optimal frequencies may be selected. The optimal frequency may then be determined based on these sub-optimal frequencies.

Because the optimal frequency is determined by balancing the treatment effects resulting from multiple parameters, the determined optimal frequency may not be optimal for a specific parameter (e.g., the steering angle). Accordingly, in various embodiments, the physical model may further predict a relationship between the peak intensity/power of the focused beam at the determined optimal frequency and the initial configurations (e.g., the sizes and/or shapes) of the transducer elements. The transducer elements may then be reconfigured to further improve the peak intensity/power at the target region. In various embodiments, at least some of the transducer elements 602 are each "partitioned" into multiple sub-regions; each sub-region may be separately activated or deactivated. For example, each sub-region may be connected to the same or different signal drivers via a corresponding channel and a corresponding switch in a switch matrix. By toggling the switches in the switch matrix, their corresponding sub-regions may be activated and deactivated. Because each of the sub-regions behaves like an independent transducer element, this may provide improved control of the geometry of the transducer array as well as improved acoustic intensity/power of the focused beam at the specific steering angle when compared with a conventional system, where the entire individual element must be active or inactive. In addition, because this approach effectively reduces the size of smallest controllable elements and increases the number of the smallest controllable elements, the steering ability of the focused acoustic beam may be significantly improved.

Accordingly, in one aspect, the invention pertains to a system for delivering ultrasound energy to a target region. In various embodiments, the system includes an ultrasound transducer having multiple transducer elements for generating a focal zone of acoustic energy at the target region; and a controller configured to (a) determine multiple sub-optimal frequencies, each associated with a parameter; (b) determine an optimal sonication frequency based at least in part on the sub-optimal frequencies for maximizing the peak acoustic intensity associated with the parameters in the focal zone; and (c) cause at least one of the transducer elements to transmit pulses at the determined optimal sonication frequency. In one implementation, a change in the parameter results in a change in the peak acoustic intensity in the focal zone and the sub-optimal frequency corresponds to a maximum of the peak acoustic intensity resulting from changes in the associated parameter.

In addition, the controller may be further configured to assign a weighting factor to each of the sub-optimal frequencies, and determine the optimal sonication frequency based at least in part on the weighting factors. In some embodiments, the controller is further configured to assign the weighting factors based on the first anatomic characteristic of the target region, the second anatomic characteristic of a non-target region located between the transducer and the target region, a steering angle of the focal zone, a contribution of each parameter to the maximum of the peak acoustic intensity, and/or retrospective data based on study of patients who have undergone ultrasound treatment. The first or the second anatomic characteristic may include, for example, a tissue type, a tissue property, a tissue structure, a tissue thickness and/or a tissue density. In one embodiment, the controller is further configured to assign the weighting factors using a machine-learning or evolutionary approach. In addition, the controller may be further configured to determine the second one of the sub-optimal frequencies based at least in part on the first one of the sub-optimal frequencies.

In various embodiments, the system further includes an imaging system, such as a computer tomography (CT) device, a magnetic resonance imaging device (MRI), a positron emission tomography (PET) device, a single-photon emission computed tomography (SPECT) device and/or an ultrasonography device, for acquiring images of the target region and/or a non-target region located between the transducer and the target region for determining one or more of the parameters. The parameters may include, for example, the first amount of acoustic energy absorption at the target region, the second amount of acoustic energy absorption at a non-target region located between the transducer and the target region, an amount of acoustic energy attenuation propagating through the non-target region, a steering angle of the focal zone and/or an area of the focal zone. Additionally, the controller may be further configured to determine, based at least in part on the images, a spatial configuration (e.g., an orientation and/or a location) of the target region with respect to the transducer. The controller can then be further configured to compute the steering angle based at least in part on the spatial configuration of the target region with respect to the transducer.

In one embodiment, the controller is further configured to determine a risk level associated with the non-target region based at least in part on the acquired images and determine the optimal sonication frequency based at least in part on the risk level. In addition, the controller may be further configured to use a physical model to predict a thermal map of the target region and/or non-target region based at least in part on the acquired images; and determine the optimal sonication frequency based at least in part on the predicted thermal map. In one implementation, the controller is further configured to compute a resonance frequency of a microbubble in the target region and determine the optimal sonication frequency based at least in part on the microbubble resonance frequency. Additionally, the controller may be further configured to determine a configuration of one or more transducer elements based at least in part on the optimal sonication frequency. The system may further include a switch matrix having multiple switches, each connected to a sub-region of a transducer element; activation of the switches may cause corresponding sub-regions to transmit pulses. The controller may then be further configured to activate one or more switches based at least in part on the determined configuration of the transducer element(s).

In another aspect, the invention relates to a method for ultrasound therapy of a target region by generating a focal zone of acoustic energy therein using an ultrasound transducer having multiple transducer elements. In various embodiments, the method includes determining multiple sub-optimal frequencies, each associated with a parameter; determining an optimal sonication frequency based at least in part on the sub-optimal frequencies for maximizing the peak acoustic intensity associated with the parameters in the focal zone; and causing one or more transducer elements to transmit pulses at the determined optimal sonication frequency. In one implementation, a change in the parameter results in a change in the peak acoustic intensity in the focal zone and the sub-optimal frequency corresponds to a maximum of the peak acoustic intensity resulting from changes in the associated parameter.

In addition, the method may further include assigning a weighting factor to each of the sub-optimal frequencies, and determining the optimal sonication frequency based at least in part on the weighting factors. In some embodiments, the weighting factors are assigned based on the first anatomic characteristic of the target region, the second anatomic characteristic of a non-target region located between the transducer and the target region, a steering angle of the focal zone, a contribution of each parameter to the maximum of the peak acoustic intensity, and/or retrospective data based on study of patients who have undergone ultrasound therapy. The first or the second anatomic characteristic may include, for example, a tissue type, a tissue property, a tissue structure, a tissue thickness and/or a tissue density. In one embodiment, the method further includes assigning the weighting factors using a machine-learning or evolutionary approach. In addition, the method may further include determining the second one of the sub-optimal frequencies based at least in part on the first one of the sub-optimal frequencies.

In various embodiments, the method further includes acquiring images of the target region and/or a non-target region located between the transducer and the target region for determining at least one of the parameters. The parameters may include, for example, the first amount of acoustic energy absorption at the target region, the second amount of acoustic energy absorption at a non-target region located between the transducer and the target region, an amount of acoustic energy attenuation propagating through the non-target region, a steering angle of the focal zone and/or an area of the focal zone. Additionally, the method may further include determining, based at least in part on the acquired images, a spatial configuration (e.g., an orientation and/or a location) of the target region with respect to the transducer. The method may include computing the steering angle based at least in part on the spatial configuration of the target region with respect to the transducer.

In one embodiment, the method includes determining a risk level associated with the non-target region based at least in part on the acquired images; and determining the optimal sonication frequency based at least in part on the risk level. In addition, the method may further include predicting a thermal map of the target region and/or non-target region based at least in part on the acquired images; and determining the optimal sonication frequency based at least in part on the predicted thermal map. In one implementation, the thermal map is predicted utilizing a physical model. The method further includes computing a resonance frequency of a microbubble in the target region; and determining the optimal sonication frequency based at least in part on the microbubble resonance frequency. Additionally, the method may further include determining a configuration of one or more transducer elements based at least in part on the optimal sonication frequency. In one embodiment, the method further includes partitioning one or more transducer elements is into multiple contiguous sub-regions, each being independently controllable to transmit pulses. The method further includes activating one or more sub-regions based at least in part on a steering angle of the focal zone.

Another aspect of the invention relates to a system for delivering ultrasound energy to a target region. In various embodiments, the system includes an ultrasound transducer having multiple transducer elements for generating a focal zone of acoustic energy at the target region, one or more transducer elements being partitioned into multiple contiguous sub-regions having a common directionality; one or more driver circuits connected to the transducer element(s); a switch matrix having multiple switches (e.g., MEMS switches and/or CMOS switches) for switchably connecting the sub-regions to the driver circuit(s), each of the sub-regions being associated with one of the switches; and a controller configured to (a) determine an optimal sonication frequency for maximizing a peak acoustic intensity in the focal zone; and (b) based at least in part on the determined optimal sonication frequency, activate one or more switches in the switch matrix for causing the corresponding sub-region to transmit ultrasound pulses to the target region.

In one implementation, the system further includes an imaging system, such as a computer tomography (CT) device, a magnetic resonance imaging device (MRI), a positron emission tomography (PET) device, a single-photon emission computed tomography (SPECT) device and/or an ultrasonography device, for acquiring images of the target region and/or a non-target region located between the transducer and the target region. The controller may then be further configured to determine, based at least in part on the acquired images, a spatial configuration (e.g., an orientation and/or a location) of the target region with respect to the transducer. In addition, the controller may be further configured to compute a steering angle of the focal zone based at least in part on the spatial configuration of the target region with respect to the transducer. In one implementation, the controller is further configured to activate the switch(es) based at least in part on the computed steering angle.

In various embodiment, the controller is further configured to determine multiple sub-optimal frequencies, each associated with a parameter, and determine the optimal sonication frequency based at least in part on the sub-optimal frequencies. In one embodiment, a change in the parameter results in a change in the peak acoustic intensity in the focal zone and the sub-optimal frequency corresponds to a maximum of the peak acoustic intensity resulting from changes in the associated parameter. In addition, the controller may be further configured to assign a weighting factor to each of the sub-optimal frequencies and determine the optimal sonication frequency based at least in part on the weighting factors. For example, the controller may be further configured to assign the weighting factors based on the first anatomic characteristic of the target region, the second anatomic characteristic of a non-target region located between the transducer and the target region, a steering angle of the focal zone, a contribution of each parameter to the maximum of the peak acoustic intensity and/or retrospective data based on study of patients who have undergone ultrasound treatment. The first or the second anatomic characteristic may include, for example, a tissue type, a tissue property, a tissue structure, a tissue thickness and/or a tissue density. Additionally or alternatively, the controller may be further configured to assign the weighting factors using a machine-learning and/or evolutionary approach. The controller may be further configured to determine the second one of the sub-optimal frequencies based at least in part on the first one of the sub-optimal frequencies.

In one embodiment, the controller is further configured to determine a risk level associated with the non-target region based at least in part on the acquired images; and determine the optimal sonication frequency based at least in part on the risk level. In addition, the controller may be further configured to use a physical model to predict a thermal map of the target region and/or non-target region based at least in part on the acquired images; and determine the optimal sonication frequency based at least in part on the predicted thermal map. In one implementation, the controller is further configured to compute a resonance frequency of a microbubble in the target region; and determine the optimal sonication frequency based at least in part on the microbubble resonance frequency.

In yet another aspect, the invention pertains to a method for ultrasound therapy of a target region by generating a focal zone of acoustic energy therein utilizing an ultrasound transducer having (i) multiple transducer elements, one or more transducer elements being partitioned into multiple contiguous sub-regions having a common directionality, (ii) one or more driver circuits connected to the transducer element(s), and (iii) a switch matrix chaving multiple switches for switchably connecting the sub-regions to the driver circuit(s), each of the sub-regions being associated with one of the switches. In various embodiments, the method includes determining an optimal sonication frequency for maximizing a peak acoustic intensity in the focal zone; and based at least in part on the determined optimal sonication frequency, activating one or more switches in the switch matrix for causing the corresponding sub-region(s) to transmit ultrasound pulses to the target region.

In one implementation, the method further includes acquiring images of the target region and/or a non-target region located between the transducer and the target region. The method may further include determining, based at least in part on the acquired images, a spatial configuration (e.g., an orientation and/or a location) of the target region with respect to the transducer. In addition, the method may further include computing a steering angle of the focal zone based at least in part on the spatial configuration of the target region with respect to the transducer. In one embodiment, the method further includes activating the switch(es) based at least in part on the computed steering angle.

Additionally, the method may further include determining multiple sub-optimal frequencies, each associated with a parameter; and determining the optimal sonication frequency based at least in part on the sub-optimal frequencies. In one embodiment, a change in the parameter results in a change in the peak acoustic intensity in the focal zone and the sub-optimal frequency corresponds to a maximum of the peak acoustic intensity resulting from changes in the associated parameter. In addition, the method may further include assigning a weighting factor to each of the sub-optimal frequencies and determining the optimal sonication frequency based at least in part on the weighting factors. For example, the method may further include assigning the weighting factors based on the first anatomic characteristic of the target region, the second anatomic characteristic of a non-target region located between the transducer and the target region, a steering angle of the focal zone, a contribution of each parameter to the maximum of the peak acoustic intensity and/or retrospective data based on study of patients who have undergone ultrasound treatment. The first or the second anatomic characteristic may include, for example, a tissue type, a tissue property, a tissue structure, a tissue thickness and/or a tissue density. Additionally or alternatively, the method may further include assigning the weighting factors using a machine-learning or evolutionary approach. In one embodiment, the method further includes determining the second one of the sub-optimal frequencies based at least in part on the first one of the sub-optimal frequencies.

In various embodiments, the method further includes determining a risk level associated with the non-target region based at least in part on the acquired images; and determining the optimal sonication frequency based at least in part on the risk level. In addition, the method may further include predicting a thermal map of the target region and/or non-target region based at least in part on the acquired images; and determining the optimal sonication frequency based at least in part on the predicted thermal map. In one implementation, the method further includes computing a resonance frequency of a microbubble in the target region; and determining the optimal sonication frequency based at least in part on the microbubble resonance frequency.

Still another aspect of the invention relates to a system for delivering ultrasound energy to a target region. In various embodiments, the system includes an ultrasound transducer having multiple transducer elements for generating a focal zone of acoustic energy at the target region, one or more transducer elements being partitioned into multiple contiguous sub-regions having a common directionality; one or more driver circuits connected to the transducer element(s); a switch matrix including multiple switches (e.g., MEMS switches and/or CMOS switches) for switchably connecting the sub-regions to the driver circuit(s), each of the sub-regions being associated with one of the switches; one or more imaging systems, such as a computer tomography (CT) device, a magnetic resonance imaging device, a positron emission tomography (PET) device, a single-photon emission computed tomography (SPECT) device and/or an ultrasonography device, for measuring a spatial configuration (e.g., an orientation and/or a location) of the target region with respect to the transducer; and a controller configured to activate one or more switches in the switch matrix to thereby cause the corresponding sub-region to transmit ultrasound pulses to the target region based at least in part on the measured spatial configuration. In one implementation, the controller is further configured to compute a steering angle of the focal zone based at least in part on the spatial configuration and activate the transducer element(s) based on the steering angle.

In another aspect, the invention relates to a method for ultrasound therapy of a target region by generating a focal zone of acoustic energy therein utilizing an ultrasound transducer having (i) multiple transducer elements, one or more transducer elements being partitioned into multiple contiguous sub-regions having a common directionality, (ii) one or more driver circuits connected to the transducer element(s), and (iii) a switch matrix including multiple switches for switchably connecting the sub-regions to the driver circuit(s), each of the sub-regions being associated with one of the switches. In various embodiments, the method includes measuring a spatial configuration (e.g., an orientation and/or a location) of the target region with respect to the transducer; and based at least in part on the measured spatial configuration, activating one or more switches in the switch matrix to thereby cause the corresponding sub-region to transmit ultrasound pulses to the target region.

As used herein, the terms "approximately," "roughly," and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing and the following detailed description will be more readily understood when taken in conjunction with the drawings, in which:

FIGS. 7A-7E depicts approaches for adjusting configurations of the transducer elements so as to maximize the peak intensity/power of a focused beam at the target region in accordance with various embodiments.

DETAILED DESCRIPTION

Figure 3:
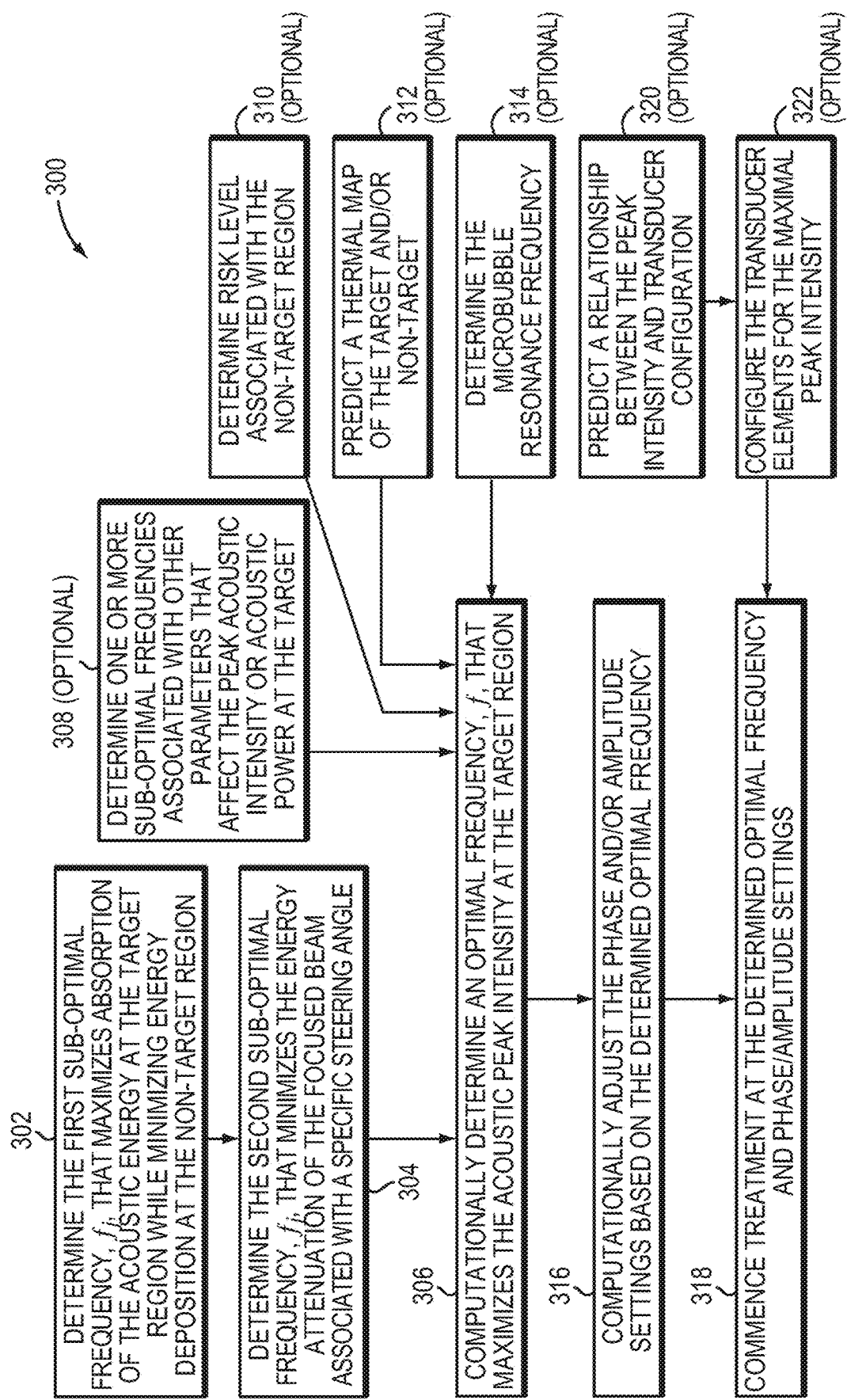
FIG. 3 is a flow chart illustrating exemplary approaches for maximizing the peak intensity or acoustic power of a focused beam in accordance with various embodiments.

Various embodiments hereof provide approaches to planning ultrasound treatments having an optimal frequency that maximizes the peak acoustic intensity or acoustic power at the target tissue, while at the same time avoiding damage to non-target tissue. FIG. 3 is a flow chart illustrating an exemplary treatment-planning approach 300 in accordance with various embodiments. As shown, treatment planning may begin, in step 302, with determining the first sub-optimal frequency, $f_j$ (or the first range of sub-optimal frequencies), with respect to a single parameter (e.g., energy absorption of the acoustic energy at the target region). Thus, sonications applied at the sub-optimal frequency $f_j$ may generate a maximal energy absorption at the target while minimizing energy deposition in the non-target region. Typically, the transducer elements are driven so that the waves converge at a focal zone in the target region. Within the focal zone, the acoustic power of the beam is (at least partially) absorbed by the tissue, thereby generating heat and raising the temperature of the tissue to a point where the cells are denatured and/or ablated. The degree of ultrasound absorption over a propagation length in tissue is a function of frequency, given by:

$$P_t = P_0 \times (1 - 10^{-2\alpha f}) 10^{-2\alpha f},$$

where $P_0$ represents the initial acoustic power of ultrasound beams emitted from the transducer; f represents the transmitting frequency of the ultrasound (measured in MHz); a represents the absorption coefficient at the relevant frequency range (measured in cm$^{-1}\cdot$MHz$^{-1}$) and may be obtained from known literature; z represents the focal length—i.e., a distance that the ultrasound beam propagates through the tissue prior to reaching the target (which is measured in cm); and $P_t$ represents the acoustic power at the target region. Accordingly, the higher the product $\alpha \cdot f$, the greater will be the degree of absorption in the target region. Additionally, the higher product $\alpha \cdot f$ corresponds to a higher fraction of ultrasound that is absorbed before it reaches the target region. Excessive energy absorption by the non-target tissue in the beam path zone may, however, cause damage thereto. As a result, choice of the ultrasound frequency reflects a trade-off between absorption of the acoustic energy along the beam path and power absorption at the target; the sub-optimal frequency, $f_j$ (or the sub-optimal frequency range), is preferably selected to provide maximal energy absorption at the target while avoiding overheating tissue in the beam path zone.

Figure 2:
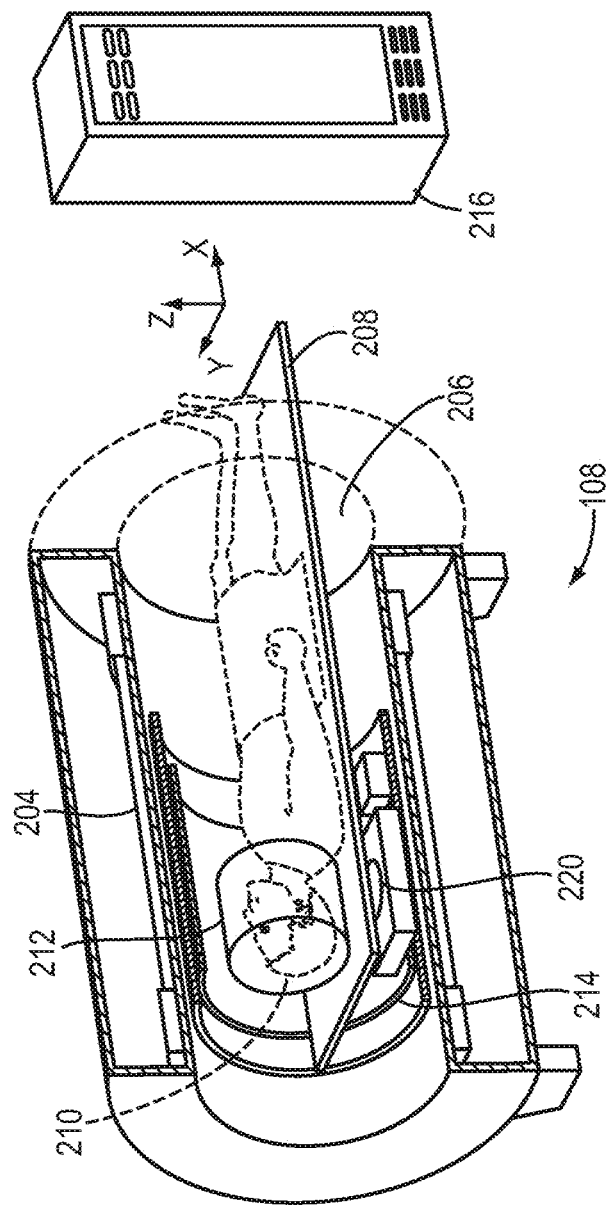
FIG. 2 illustrates an MRI system in accordance with various embodiments.
Figure 4:
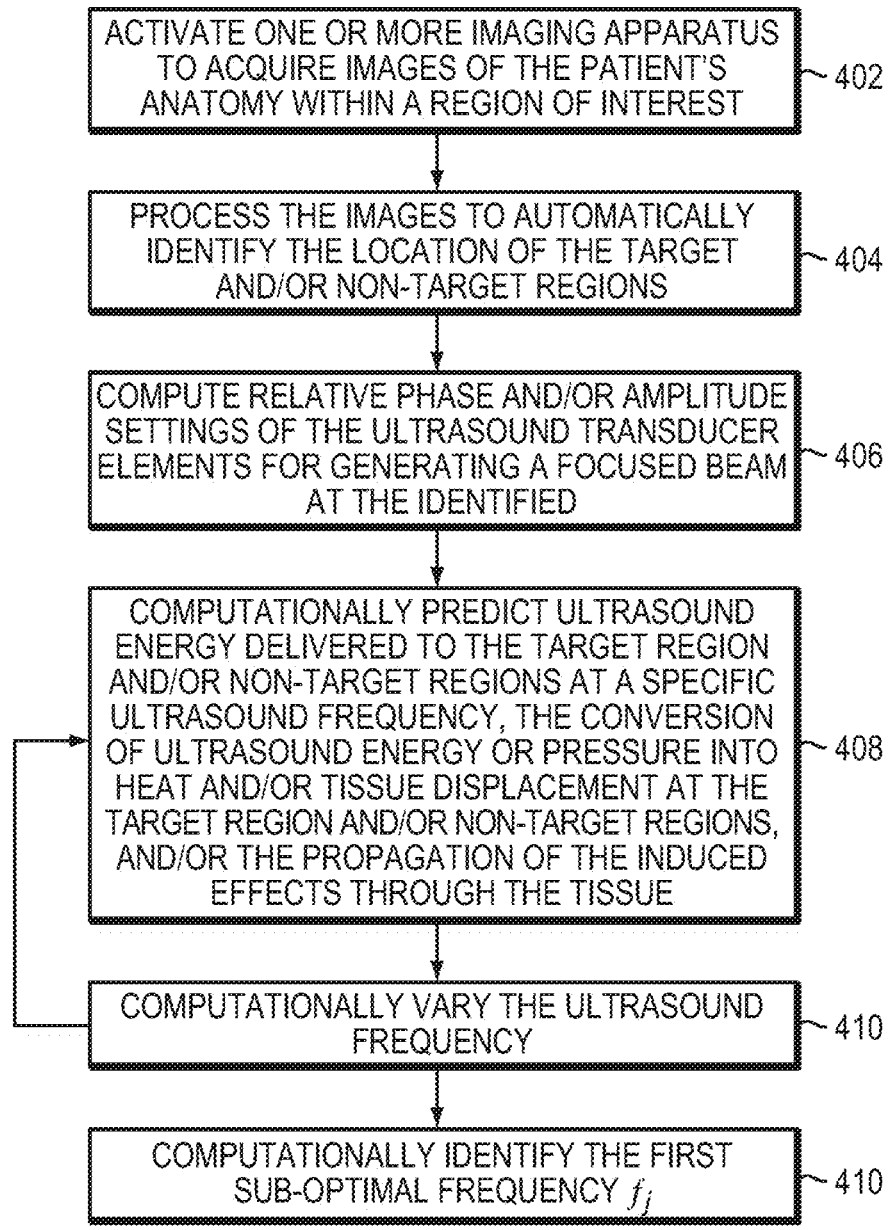
FIG. 4 is a flow chart illustrating an exemplary approach for determining a sub-optimal sonication frequency that maximizes absorption of the acoustic energy at the target region in accordance with various embodiments.

FIG. 4 depicts an exemplary approach for determining the sub-optimal frequency $f_j$ in accordance with various embodiments. In a first step 402, one or more imaging apparatus is activated to acquire images of the patient's anatomy within a region of interest. The images may be 3D images or a set of 2D image slices suitable for reconstructing 3D images of the anatomic region of interest. The imaging device may include, for example, the MRI apparatus 108 (as depicted in FIG. 2), a computer tomography (CT) device, a positron emission tomography (PET) device, a single-photon emission computed tomography (SPECT) device, or an ultrasonography device. In step 404, the images are processed by a controller associated with the imaging apparatus to automatically identify therein the location of the target and/or non-target regions using suitable image-processing techniques. Then, relative phase and/or amplitude settings of the ultrasound transducer elements that result in a beam focused at the identified target region may be computed (step 406). This step generally utilizes a physical model and takes into account the geometry as well as the position and orientation of the ultrasound transducer relative to the target region, as well as any a-priori knowledge and/or image-derived information about the intervening tissues. In some embodiments, different imaging apparatus are involved in determining the relative position of the target with respect to the transducer elements. For example, the orientations and locations of the transducer elements may be obtained using, e.g., a time-of-flight approach in the ultrasound system, whereas the spatial characteristics of the target region may be acquired using MRI. As a consequence, it may be necessary to register coordinate systems in different imaging modalities prior to computing the expected amplitude and/or phase associated with each transducer element. Exemplary registration approaches are provided, for example, in U.S. Pat. No. 9,934,570, the entire disclosure of which is hereby incorporated by reference.

In addition, the physical model may include anatomic characteristics (e.g., the type, property, structure, thickness, density, etc.) and/or material characteristics (e.g., the energy absorption of the tissue at a specific frequency or the speed of sound) of the intervening tissue located in the beam path zone between the transducer and the target region in order to predict and correct for beam aberrations resulting therefrom. In one implementation, the anatomic characteristics of the intervening tissue are acquired using the imaging device. For example, based on the acquired images of the anatomic region of interest, a tissue model characterizing the material characteristics of the target and/or non-target regions may be established. The tissue model may take the form of a 3D table of cells corresponding to the voxels representing the target and/or non-target tissue; the values of the cells represent characteristics of the tissue, such as the speed of sound, that are relevant to aberrations that occur when the beam traverses the tissue. The voxels are obtained tomographically by the imaging device and the type of tissue that each voxel represents can be determined automatically by conventional tissue-analysis software. Using the determined tissue types and a lookup table of tissue parameters (e.g., speed of sound by type of tissue), the 3D table of the tissue model may be populated. Further detail regarding creation of a tissue model that identifies the speed of sound, heat sensitivity and/or thermal energy tolerance of various tissues may be found in U.S. Patent Publication No. 2012/0029396, the entire disclosure of which is hereby incorporated by reference.

In step 408, based on the relative phase and/or amplitude settings of the ultrasound transducer elements and the anatomic and/or material characteristics of the target/non-target tissue, the physical model may computationally predict ultrasound energy delivered to the target region and/or non-target regions at a specific ultrasound frequency, the conversion of ultrasound energy or pressure into heat and/or tissue displacement at the target region and/or non-target regions, and/or the propagation of the induced effects through the tissue. Typically, the simulation takes the form of (or includes) differential equations. For example, the physical model may consist of or include the Pennes model and a bioheat equation to simulate heat transfer in tissue. Approaches to simulating the sonications and their effects on the tissue are provided, for example, in U.S. Patent Publication No. 2015/0359603, the entire disclosure of which is hereby incorporated by reference.

As described above, because the degree of ultrasound absorption at the target and the induced effects at the target region and/or non-target regions depend on the applied ultrasound frequency, in one embodiment, the physical model computationally varies the ultrasound frequency and predict the energy absorption and the induced effects at the target region and/or non-target regions associated therewith (step 410). In some embodiments, the physical model applies various "test frequencies" within a "test range" of frequencies. The test range may span the entire range of frequencies suitable for ultrasound treatment (e.g., in various embodiments, 0.1 MHz to 10 MHz), but is typically a much smaller sub-range thereof that is expected to include the sub-optimal frequency $f_j$. Such a sub-range may be determined, e.g., based on computational estimates of the sub-optimal frequency $f_j$, the results of simulations, or empirical data acquired for the same organ or tissue in another patient. The frequencies to be tested may be distributed uniformly or non-uniformly over the test range. In various embodiments, the density of test frequencies increases with closer proximity to an estimated sub-optimal frequency. In addition, the test range and the test frequencies therein may be predetermined, or adjusted dynamically during the simulation process. For example, in one embodiment, computational testing is initially performed at large frequency intervals (e.g., in steps of 20 kHz) over a large test range (e.g., from 600 to 750 kHz) to determine a sub-range of frequencies resulting in high energy absorption at the target, and the sub-optimum frequency $f_j$ is thereafter determined within the sub-range by computational testing at smaller intervals (e.g., in steps of 10 kHz or 5 kHz). In another embodiment, testing is performed for a sub-set of pre-determined potential test frequencies, each actual test frequency being selected from the set of potential test frequencies based on the results of previous tests. Based on the simulation results, the test frequency corresponding to the maximal energy absorption at the target may then be identified as the sub-optimal frequency $f_j$ (step 412).

Figure 5A:
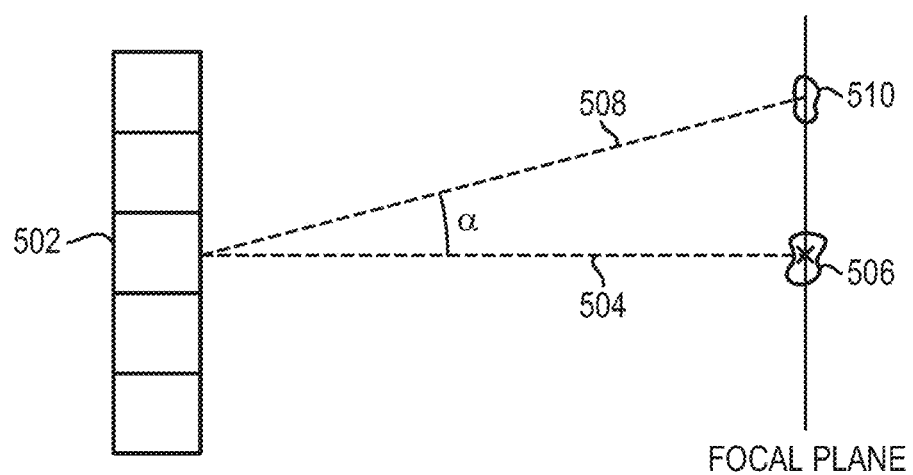
FIG. 5A illustrates the principle of electronic steering of a two-dimensional planar transducer array having multiple transducer elements in accordance with various embodiments.

Referring again to FIG. 3, in step 304, the second sub-optimal frequency, $f_i$, that minimizes the energy attenuation of the focused beam propagating toward the target region resulting from a specific steering angle is determined. FIG. 5A illustrates the principle of electronic steering of a two-dimensional planar transducer array that includes multiple transducer elements 502. In particular, the "steering angle" of any one transducer element of the array is the angle α between the first focal axis 504 extending generally orthogonally from the element to an "unsteered" focal zone 506 at which the element 502 contributes a maximum possible power, and a second focal axis 508 extending from the transducer element 502 to a "steered-to" focal zone 510 located at the target region. The "steering ability" of the transducer array is defined as a steering angle α at which energy delivered to the steered-to focal zone 510 falls to half of the maximum power delivered to the unsteered focal zone 506. Notably, the steering angle α of each transducer element of a phased array may be different, but as the distance from the elements to the focal zone increases, the respective steering angles for the array elements approach the same value. In practice, because the distance between the transducer array and the target region is sufficiently longer than the distance between the transducer elements, the steering angles associated with the transducer elements in the array can be considered the same.

Figure 5B:
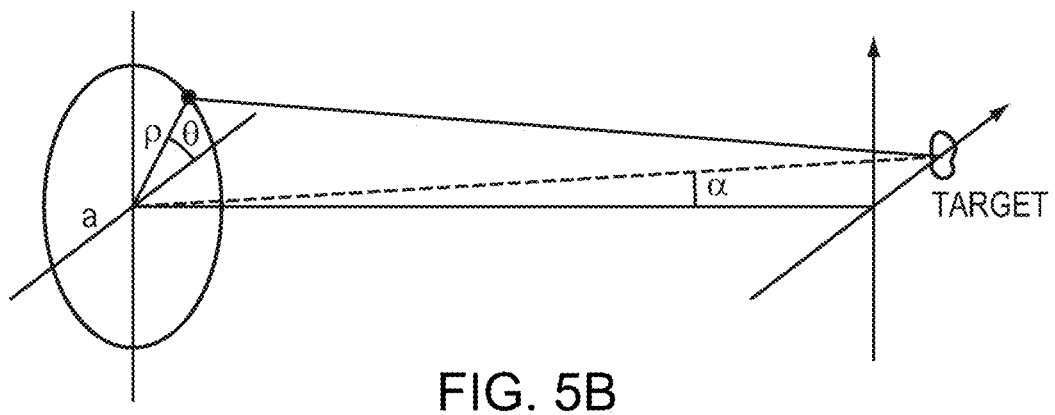
FIGS. 5B and 5C schematically illustrate the geometry for determining directivity of a circular transducer element and a rectangular transducer element, respectively, in accordance with various embodiments.
Figure 5C:
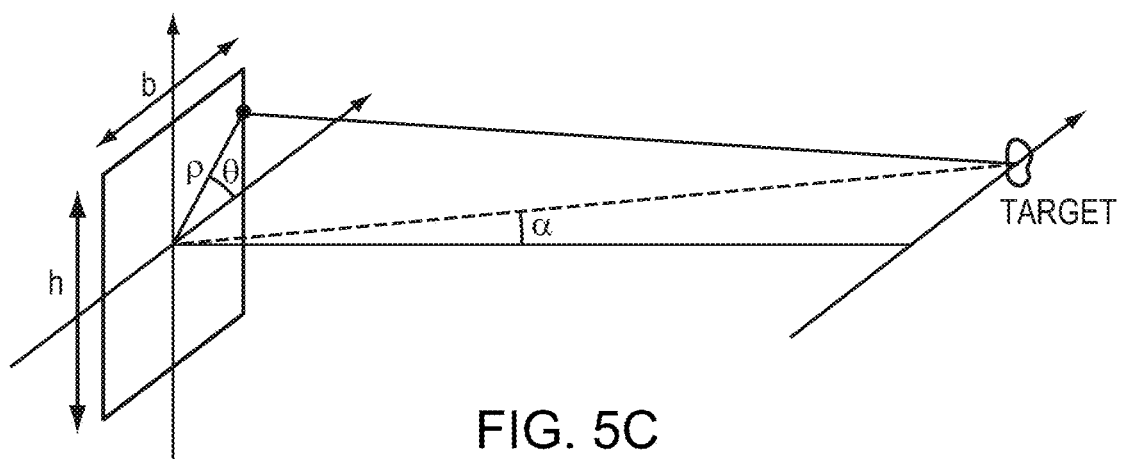

In addition, from a physical point of view, a single transducer element emits a wave in the form of a spreading beam. The angular distribution of this spreading beam is called "directivity." Typically, the peak intensity/power of the acoustic beam at the focal zone positively correlates to the directivity, D, thereof. Referring to FIG. 5B, the directivity, $D_c$, of a circular transducer having a radius a, is given by:

$$D_c(\alpha) = \frac{2J_1(ka \cdot \sin \alpha)}{ka \cdot \sin \alpha}$$

where $\alpha$ represents the steering angle; $J_1$ represents the Bessel function of the first kind with order 1; k represents the propagation constant of the acoustic waves (i.e., $k=2\pi/\pi \propto f$, where $\lambda$ is the wavelength). Similarly, referring to FIG. 5C, the directivity, $D_r$, of a rectangular transducer having dimensions b×h is a sinc function given by:

$$D_r(\alpha) = sinc\left(\frac{kb \cdot \sin \alpha \cos \theta}{2}\right) \cdot sinc\left(\frac{kb \cdot \sin \theta \cos \alpha}{2}\right)$$

where $\theta$ denotes one of the coordinates of a transducer element in the plane of the transducer surface. Accordingly, the energy attenuation resulting from the steering angle $\alpha$ of the focused beam may depend on the sonication frequency.

Figure 5D:
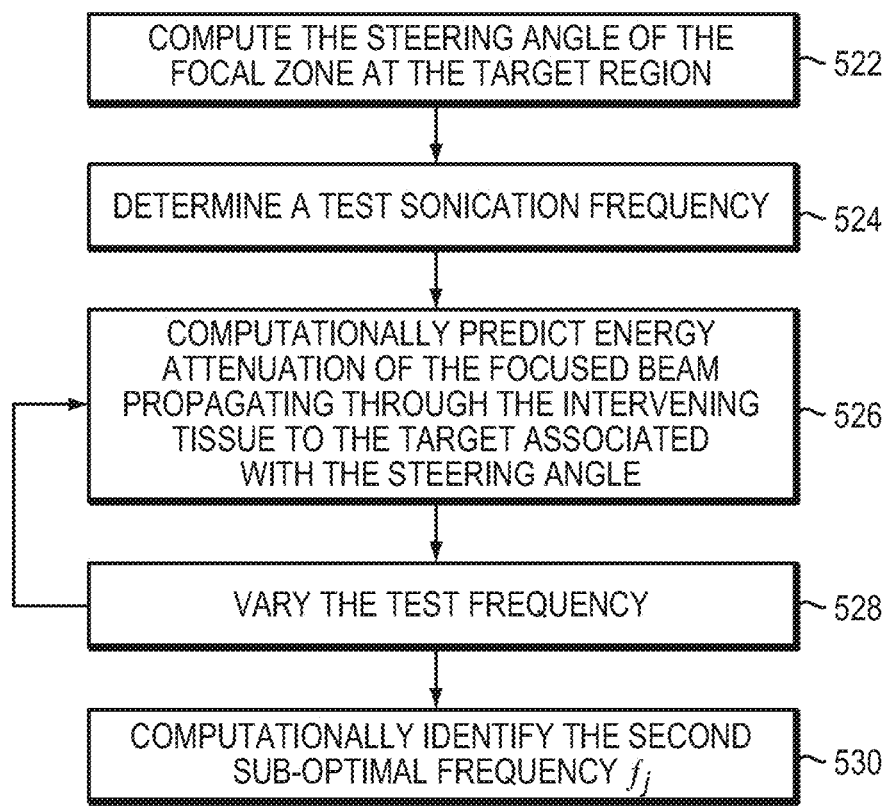
FIG. 5D is a flow chart illustrating an exemplary approach for determining a sub-optimal frequency that minimizes energy attenuation of the steered beam having a specific steering angle in accordance with various embodiments.

FIG. 5D depicts an exemplary approach for determining the sub-optimal frequency $f_i$ that minimizes the energy attenuation of the steering beam at the focal zone having a specific steering angle in accordance with various embodiments. In a first step 522, the steering angle of the focal zone at the target is computed based on the spatial arrangement (e.g., positions and orientations) of the ultrasound transducer elements 104 with respect to the target region. Again, the spatial arrangement may be determined based on, for example, the images acquired using the imaging apparatus, time-of-flight approach and/or image registration described in step 402. In a second step 524, ultrasound waves/pulses having a test frequency in a test range may be computationally applied to sonicate the target region. In one implementation, the test range and/or frequencies in step 524 are defined based on the sub-optimal frequency $f_j$ corresponding to maximal energy absorption at the target determined in step 302. For example, the determined sub-optimal frequency $f_j$ may serve as the central frequency in the test range and the test range may include frequencies distributed uniformly or non-uniformly over a range of $f_j \pm \Delta f$, where $\Delta f$ is 5% (or, in some embodiments, 10% or 20%) of $f_j$. Alternatively, the test range may span the entire range of frequencies suitable for ultrasound treatment. Again, the sub-range may be determined based on, for example, computational estimates of the optimal frequency $f_i$, the results of simulations, or empirical data acquired for the same organ or tissue in another patient; and adjustment thereof may be dynamically performed during the simulation process as described above for determining the optimal frequency $f_j$. In step 526, the physical model may then predict energy attenuation of the focused beam propagating through the intervening tissue to the target region associated with the steering angle computed in step 522. Because the acoustic power at the focal zone depends on the steering angle and the sonication frequency, in one embodiment, the physical model may vary the sonication frequency and predict energy attenuation associated with the updated frequency at the steering angle (step 528). In step 530, the test frequency that corresponds to the minimal energy attenuation at the determined steering angle is identified as the sub-optimal frequency $f_i$.

Accordingly, the treatment planner has taken into account at least two parameters that may significantly affect the acoustic power or peak intensity at the target region—i.e., the anatomic/material characteristics of the target and/or non-target tissue (by determining the sub-optimal frequency $f_j$ associated with maximal energy absorption at the target region) and the specific steering angle of the focal zone (by determining the sub-optimal frequency $f_i$ associated with minimal energy attenuation of the focused beam traversing the intervening tissue). The two sub-optimal frequencies $f_j$ and $f_i$ may or may not be the same. If they are different, choice of the optimal sonication frequency reflects a trade-off between the absorption of the acoustic energy in the path zone, the power absorption at the target, and the energy attenuation resulting from beam propagation at a specific steering angle. Referring again to FIG. 3, in various embodiments, the treatment planner may then, based on the determined sub-optimal frequencies $f_j$ and $f_i$, determine an optimal frequency f that maximizes the acoustic peak intensity at the target region (step 306). For example, if the second sub-optimal frequency $f_i$ is determined by varying the frequency over the test range between $f_j - \Delta f$ and $f_j + \Delta f$, and $f_i$ corresponds to the minimal energy attenuation at the specific steering angle within this test range, the planner may determine that the optimal frequency f is $f_i$.

Alternatively, the treatment planner may assign a weighting factor to each of the sub-optimal frequencies $f_j$ and $f_i$ and then determine the optimal frequency f based on the weighted average thereof. The weighting factors may be assigned based on, for example, the tissue type of the target and/or non-target tissue, the steering angle, prior knowledge, and the degree of impact on the parameter (e.g., energy absorption at the target and/or energy attenuation at the specific angle) resulting from the change of the frequency. Generally, a larger impact indicates that the sub-optimal frequency associated therewith is more important for achieving the maximal peak intensity/power at the target region; thus, a larger weighting factor may be assigned thereto. For example, when adjusting the sonication frequency results in a significant decrease in energy absorption at the target region but only minor increase of energy attenuation at the steering angle of the focused beam onto the target region, the treatment planner may assign a larger weighting factor to the frequency $f_j$ (that takes into account the energy absorption in the beam path zone and target region) and a smaller weighting factor to the frequency $f_i$ (that takes into account the energy attenuation at the steering angle) for computing the optimal frequency f. Conversely, if adjustment of the sonication frequency results in a significant increase of the energy attenuation at the specific steering angle of the focal zone, a larger weighting factor may be assigned to the frequency $f_i$.

In some embodiments, the tissue types and their associated absorption coefficients (or attenuation coefficients) and the steering angles of the focal zone and their associated energy attenuations at relevant frequencies (e.g., frequencies suitable for ultrasound treatment) may be obtained empirically prior to and/or during ultrasound treatment, using numerical simulations (e.g., implementing the physical model) and/or based on known literature; this information may be stored as a lookup table in a database and may be retrieved when determining the weighting factors assigned to the frequencies $f_j$ and $f_i$.

Additionally or alternatively, the weighting factors of the frequencies $f_j$ and $f_i$ may be assigned based on a retrospective study of the patients who have undergone the ultrasound treatment procedures. For example, the treatment planner may compute the two sub-optimal frequencies $f_j$ and $f_i$ based on, for example, the acquired images of the patients as described above. Then, based on the computed frequencies $f_j$ and $f_i$ and the sonication frequency that was empirically determined during treatment or applied for treatment, the weighting factors associated with $f_j$ and $f_i$ can be determined. Different patients may have different anatomic/material characteristics of the target/non-target regions and thus different weighting factors may be assigned to $f_j$ and $f_i$. Again, the anatomic/material characteristics of the patients who have undergone ultrasound treatment together with the associated weighting factors may be stored as a lookup table in a database. Prior to or during treatment of a new patient, the new patient's anatomic/material characteristics may be compared against the stored data; and based on the similarity therebetween, the stored anatomic/material characteristics that best match the new patient's anatomic/material characteristics can be identified. Subsequently, the weighting factors assigned to the best-matching anatomic/material characteristics can be assigned to the frequencies $f_j$ and $f_i$ of the new patient for determining the optimal treatment frequency f.

In some embodiments, the weighting factors assigned to the frequencies $f_j$ and $f_i$ may be obtained using a conventional learning or evolutionary algorithm. For example, the anatomic/material characteristics of the patients who have undergone the ultrasound treatment procedures and the frequencies that were applied for treating these patients and/or the sub-optimal frequencies $f_j$ and $f_i$ computed using the physical model may be included in a training set. A relationship between the observed anatomic/material characteristics and the weighting factors assigned to the frequencies $f_j$ and $f_i$ can then be determined, for example, using a machine learning process, such as regression, classification, decision tree learning, association rule learning, similarity learning, supervised learning, unsupervised learning, online learning, etc., as understood by those skilled in the art and implemented without undue experimentation based on the training set. Alternatively, the training set may be used to train a neural network, which assigns weights to the inputs (the anatomic/material characteristics, for example) as well as to various intermediate nodes, and refines these weights using backpropagation. The frequencies $f_j$ and $f_i$ represent the output of the neural network and may be predicted for a new patient using the trained neural network. Approaches to training a neural network are provided, for example, in International Application No. PCT/IB2017/001029 (filed on Jul. 14, 2017), the entire disclosure of which is hereby incorporated by reference.

It should be noted that the approaches to determining the weighting factors assigned to the frequencies $f_j$ and $f_i$ described herein are presented as representative examples; any other approaches suitable for determination of the weighting factors may be utilized and are thus within the scope of the present invention.

Figure 5E:
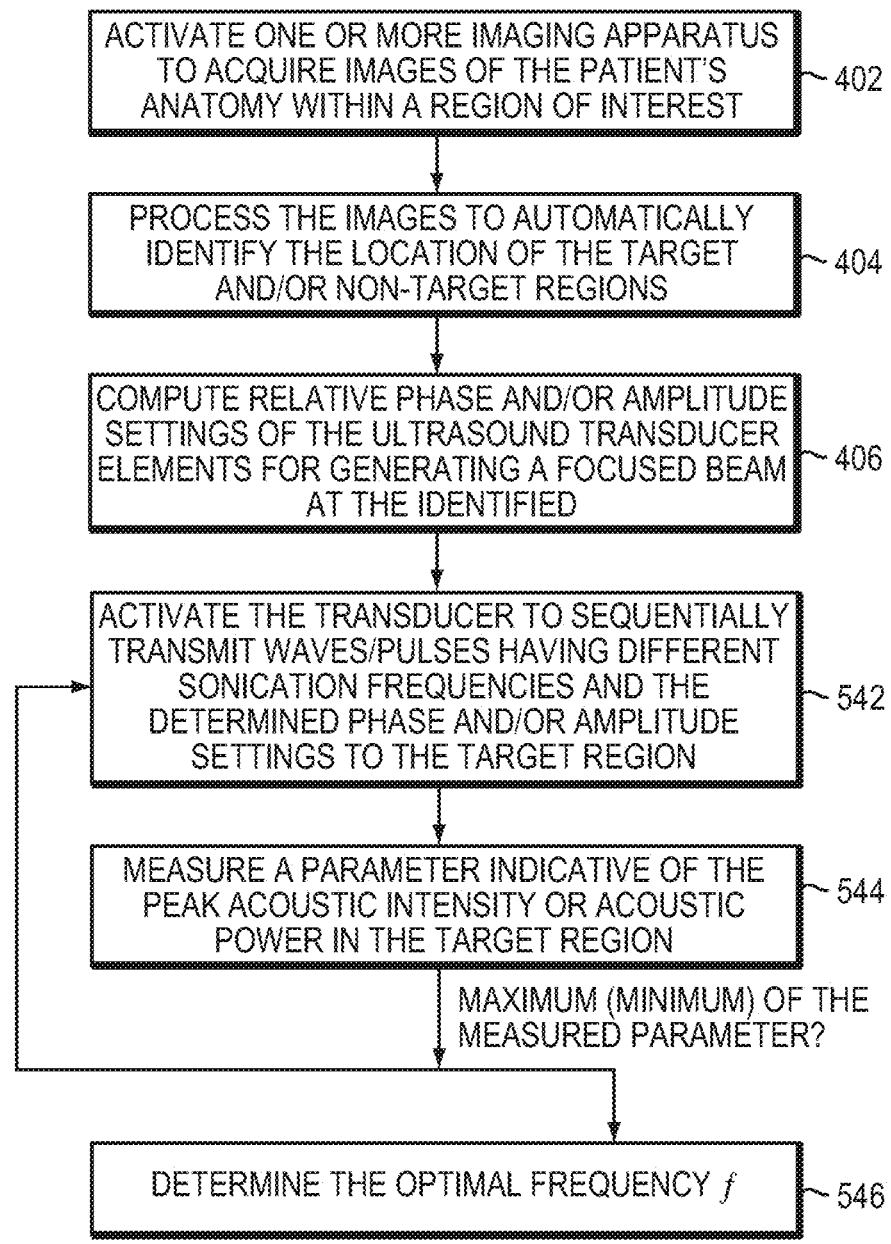
FIG. 5E is a flow chart illustrating an exemplary approach for empirically determining an optimal frequency for maximizing the peak acoustic intensity/power of a focused beam in accordance with various embodiments.

Alternatively, the optimal frequency f may be empirically determined. For example, referring to FIG. 5E, after the relative phase and/or amplitude settings of the ultrasound transducer elements that result in a beam focused at the identified target region are determined (step 406), the transducer array may sequentially transmit waves/pulses having different sonication frequencies (e.g., applying the test frequencies within the test range) and the determined phase and/or amplitude settings to the target region (step 542). For each test frequency, a parameter indicative of the peak acoustic intensity/power in the target region may be measured using, e.g., MRI thermometry (which measures the temperature increase in the target resulting from the acoustic energy), MR-ARFI (which measures the tissue displacement resulting from acoustic pressure at the target), ultrasound reflection detection (which measures the intensity of the ultrasound that is reflected), or generally any experimental technique that measures a parameter correlating with the peak intensity at the target in a known and predictable manner (step 544). Steps 542 and 544 may be iteratively performed until the maximum (in the case of, e.g., temperature or pressure) or minimum (in the case of, e.g., reflection) of the measured parameter is measured. Again, the test frequency corresponding to the maximum (in the case of, e.g., temperature or pressure) or minimum (in the case of, e.g., reflection) of the measured parameter is then determined as the optimal frequency f (step 546).

Various techniques can be used to measure the acoustic intensity/power in the target directly or indirectly via a related physical quantity—to then maximize the peak intensity/power via selection of the optimal frequency f. One approach is to monitor the temperature at the target, which increases proportionally to the amount of acoustic energy deposited therein. Thermometry methods may be based, e.g., on MRI, and may utilize a system such as that depicted in FIG. 2, in conjunction with suitable image-processing software. Among various methods available for MR thermometry, the proton resonance frequency (PRF) shift method is often the method of choice due to its excellent linearity with respect to temperature change, near-independence from tissue type, and temperature map acquisition with high spatial and temporal resolution. The PRF shift method exploits the phenomenon that the MR resonance frequency of protons in water molecules changes linearly with temperature. Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image after the temperature change, thereby capturing a small phase change that is proportional to the change in temperature. A map of temperature changes may then be computed from the MR images by determining, on a pixel-by-pixel basis, phase differences between the baseline image and the treatment image, and converting the phase differences into temperature differences based on the PRF temperature dependence while taking into account imaging parameters such as the strength of the static magnetic field and echo time (TE) (e.g., of a gradient-recalled echo). Various alternatives or advanced methods may be used to compensate for patient motion, magnetic-field drifts, and other factors that affect the accuracy of PRF-based temperature measurements; suitable methods known to those of skill in the art include, e.g., multibaseline and referenceless thermometry.

Using PRF-based or any other suitable thermometry method, the optimal ultrasound frequency within a specified range can be determined by driving the transducer successively at a number of different frequencies (e.g., at specified frequency intervals within the selected range), while keeping the power and duration (or, more generally, the total transmitted energy) the same, to focus ultrasound at the target site of a particular patient, and measuring the temperature increase at the target for each such sonication. This is done prior to treatment; thus, in order to avoid tissue damage, the ultrasound transducer is driven at much lower power than subsequently during treatment (while being high enough to obtain meaningful signals). Further, to ensure the comparability of the measurements for different frequencies, each temperature increase is preferably measured against a similar baseline temperature. This can be accomplished by waiting a sufficient amount of time following each sonication to let the tissue cool back down to a temperature approximately equal to the baseline temperature and using sufficiently low energy such that effects on the tissue due to temperature changes are limited (e.g., clinically insignificant). When the temperature increase has been measured at the various discrete frequencies within the range of interest, the frequency for which the temperature increase is maximum is selected for operating the transducer during subsequent treatment.

Another quantity usefully related to ultrasound energy absorption in tissue is the temporary local displacement of that tissue due to acoustic radiation pressure, which is highest at the focus (where the waves converge and highest intensity is achieved). The ultrasound pressure creates a force that displaces the tissues in a way that directly reflects the acoustic field. The displacement field can be visualized, using a technique such as MR-ARFI, by applying transient-motion or displacement-sensitizing magnetic field gradients to the imaging region by gradient coils, which are part of standard MRI apparatus (such as apparatus 108 depicted in FIG. 2) and are typically located near the cylindrical electromagnet 204. When the ultrasound pulse is applied in the presence of such gradients, the resulting displacement is directly encoded into the phase of the MR response signal. For example, the gradient coils and transducer may be configured such that the ultrasound pulse pushes material near the focus towards regions of the magnetic field with higher field strengths. In response to the resulting change in the magnetic field, the phase of the MR response signal changes proportionally, thereby encoding in the signal the displacement caused by the ultrasound radiation pressure. Further detail about MR-ARFI is provided in U.S. Pat. No. 8,932,237, the entire disclosure of which is hereby incorporated herein by reference.

Referring again to FIG. 3, in various embodiments, other parameters that may affect the peak acoustic intensity/power at the target region are also taken into account when determining the optimal frequency f for treatment (step 308). For example, the focal area, A, negatively correlates to the peak acoustic intensity, I, in the focal zone, satisfying:

$$I \times A = P_t,$$

where $P_t$ represents the acoustic power of ultrasound beam in the focal zone. In addition, the area of the focal zone depends on the sonication frequency, given by:

$$A = 2\pi \left(1.22 \times \frac{\lambda}{d} \times R\right)^2,$$

where A represents the area of the focal zone for a circular transducer; $\lambda$ represents the wavelength of the ultrasound ($\lambda = 2\pi/f$); d represents the diameter of the transducer elements, and R represents the focal length. Therefore, at a given focal depth, increasing the sonication frequency may result in decrease of the focal area, which then increases the peak acoustic intensity. Accordingly, choice of the ultrasound frequency at a given focal depth involves balance between the power absorption in the beam path zone, the power absorption at the target, the energy attenuation propagating through the intervening tissue at the specific steering angle, and the peak intensity at the focal zone. In some embodiments, these parameters are sequentially evaluated to determine the optimal frequency f. For example, after the frequency that is determined by taking into account the power absorption at the target region and in the beam path zone and the steering angle as described above is determined, the treatment planner may determine the sub-optimal frequency $f_k$ corresponding to minimal focal area in the target region. Based on $f_k$ and the frequency that takes into account both the power absorption and the steering angle, the optimal frequency f can be determined using the approaches described above (e.g., assigning weighting factors thereto). Alternatively, the treatment planner may evaluate all parameters affecting the peak intensity/power at the target region at once and then determine the optimal ultrasound frequency f. For example, the optimal frequency f may be obtained by assigning weighting factors to $f_j$, $f_i$, and $f_k$ using the approaches described above.

In some embodiments, when determining the optimal frequency f, the treatment planner further considers a risk level associated with the non-target region based on the type and/or location thereof (step 310), imposing additional constraints in obtaining the optimal frequency to account for the risk level. For example, if the non-target organ next to the target region is a sensitive and/or important organ, the risk of damaging the non-target organ is high. Consequently, in this situation, the treatment planner may specify a maximum dose of acoustic energy that can be deposited in the non-target organ; selection of the optimal frequency is then constrained by the requirement of satisfying this condition. Alternatively, the frequency $f_i$ associated with minimal (or tolerable) damage to the non-target organ may be computationally determined using, for example, the physical model; a relatively large weighting factor (compared with those assigned to $f_j$, $f_i$, and/or $f_k$) may then be assigned to the frequency $f_i$ for determining the optimal frequency f for treatment. In one implementation, the frequency $f_m$ that maximizes the ratio of the acoustic intensity at the target region to the acoustic intensity at the non-target organ is predicted. Again, the optimal frequency f may then be determined based on the predicted frequency $f_m$ (e.g., by assigning a weighting factor thereto). In one embodiment, the predicted frequency $f_m$ is the optimal sonication frequency f applied during treatment.

Additionally or alternatively, the treatment planner may optimize the frequency f based on the thermal map of the target and/or non-target regions. For example, as described above, the physical model may first simulate the acoustic energy deposited on the target/non-target regions based on the geometric information of the transducer and the target and the anatomic/material properties of the target/non-target tissue. The physical model may then include the tissue model associated with the target/non-target tissue, the Pennes model and bioheat equation to simulate heat transfer in the target/non-target tissue resulting from the acoustic energy deposited thereon, thereby creating a thermal map (step 312). The physical model may sequentially vary the sonication frequency (e.g., applying test frequencies in the test range) and predict the thermal map associated therewith. In some embodiments, the optimal frequency f is selected such that the temperature at the target region achieves a desired object for treatment while the temperature at the non-target region is below the maximal temperature that the non-target tissue can tolerate without damage thereto.

In various embodiments, the ultrasound treatment procedures involve application of microbubbles. For example, the microbubbles may be generated and/or introduced to facilitate auto-focusing and/or assist the treatment (e.g., by enhancing energy absorption and/or tissue permeability at the focal zone, inducing disruption of the blood-brain barrier for targeted drug delivery when treating a neurological disorder, etc.). Because the microbubbles may oscillate at a resonance frequency in response to the applied acoustic field, thereby affecting the therapeutic effect at the target/non-target region, it may be desired to adjust the ultrasound frequency so as to enhance the treatment effects at the target while limit the microbubble response at the non-target region. Accordingly, in some embodiments, the microbubble resonance frequency may be determined and taken into account in the process of optimizing the ultrasound frequency (step 314). For example, the sonication frequency may be preferably substantially smaller (or, in some embodiments, larger) than (e.g., by a factor of ten) the microbubble resonance frequency. Approaches to determining the microbubble resonance frequency are provided, for example, in International Application No. PCT/IB2018/000841 (filed on Jun. 29, 2018), the entire disclosure of which is hereby incorporated by reference.

Accordingly, various embodiments of the present invention provide approaches for optimizing the ultrasound frequency so as to achieve the treatment goal—i.e., maximizing the peak acoustic intensity/power at the target while minimizing the exposure of non-target tissue to ultrasound. Because the peak acoustic intensity may depend on multiple parameters (such as absorption of the acoustic beam at the target tissue and non-target tissue in the beam path zone, the steering angle, and the focal area of the focal zone, etc.) that are frequency dependent, some embodiments sequentially evaluate each of these parameters and determine the sub-optimal frequency associated therewith; the optimal frequency for treatment is then determined from these sub-optimal frequencies. For example, each sub-optimal frequency may be assigned a weighting factor corresponding to its contribution toward the desired treatment goal; the optimal frequency can then be computed as the weighted sum of the sub-optimal frequencies. Alternatively, the treatment planner may evaluate these parameters simultaneously and then numerically determine the optimal frequency by assigning each parameter-associated sub-optimal frequency with a weighting factor based on its importance for achieving the treatment goal as described above.

It should be noted that the approaches for determining the optimal ultrasound frequency f described herein are presented as representative examples only; any other approaches involving evaluating multiple parameters affecting the peak acoustic intensity/power at the target region and then determining the optimal sonication frequency based on the evaluation may be implemented and are thus within the scope of the present invention. In addition, the frequency optimization may be based other parameters, such as the simulated thermal map of the target/non-target regions during treatment, the resonance frequency of microbubbles, etc.

Still referring to FIG. 3, optionally, following frequency optimization, the phase and/or amplitude settings of the phased-array transducer may be adjusted to optimize the focus for the determined optimal frequency (step 316). Treatment may then commence at the optimal frequency and phase/amplitude settings (step 318). It should be noted, however, that because the optimal frequency f is determined by balancing various parameters affecting the peak intensity/power at the focal zone, the determined optimal frequency f may not be optimal for a specific parameter (such as the steering angle). Accordingly, in various embodiments, the treatment planner may utilize the physical model to predict a relationship between the peak intensity of the focused beam at the determined optimal frequency f and the configurations (e.g., the sizes and/or shapes) of the transducer elements (step 320). Based thereon, the transducer elements may then be configured to further improve the peak intensity at the target region (step 322).

Figure 6A:
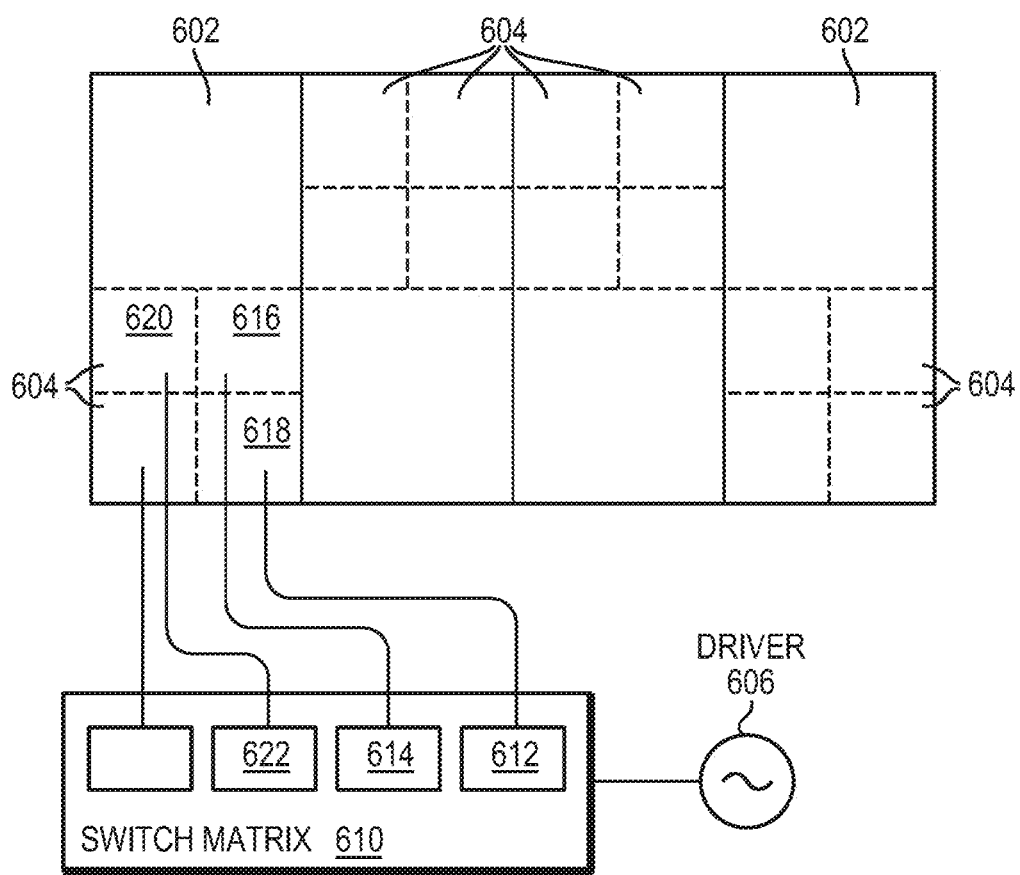
FIGS. 6A and 6B schematically illustrate approaches of partitioning individual transducer elements in accordance with various embodiments.

For example, referring to FIG. 6A, in various embodiments, at least some of the transducer elements 602 are each "partitioned" into multiple sub-regions 604, each of which may be separately activated or deactivated. In one embodiment, each of these sub-regions can be selectively driven (or not driven) by the same driver signal 606 (e.g., having a single frequency and a single phase value) or, alternatively, different driver signals (e.g., having different frequencies and/or different phase values). In the illustrated configuration, each sub-region 604 of the element is connected to the signal driver 606 via a corresponding channel 608 and a corresponding switch (e.g., a MEMS switch or a CMOS switch) in a switch matrix 610. Thus, setting the states of the switches in the switch matrix determines whether their corresponding sub-regions are active or inactive. Because each of the sub-regions 604 behaves approximately as an independent transducer element, this approach provides improved control of the geometry of the transducer array and its output compared with the system 100 in which the entire individual element 102 must be active or inactive. For example, when switches 612, 614 are closed, sub-regions 616, 618 of the transducer element are activated to transmit waves/pulses. As a result, the shape of the transducer element is effectively changed from a square to a rectangle, and the size is horizontally reduced to ½ the original size (i.e., the size of the transducer element 602); this may enhance horizontal steering of the acoustic beam. Similarly, by closing the switches 614, 622, sub-regions 616, 620, respectively, are activated for enhancing vertical steering; and by closing the switches 612, 622, sub-regions 618, 620, respectively, are activated for enhancing diagonal steering.

Figure 6B:
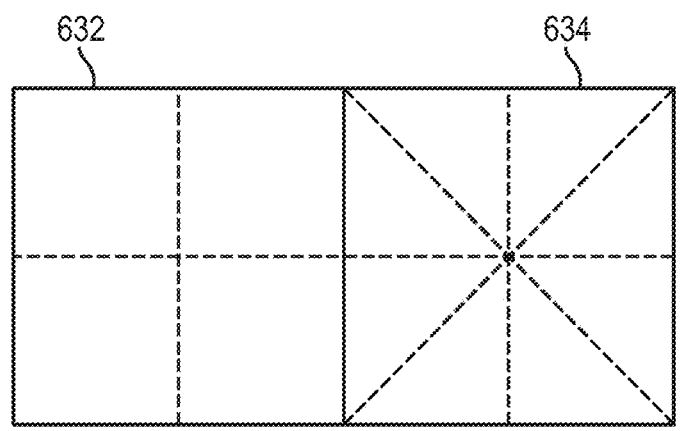

It should be noted that the number and shape of the sub-regions within each transducer element described herein are presented as representative examples only; each transducer element may be partitioned into any number of sub-regions having any shapes as long as that all sub-regions within an individual transducer element have the same directionality—i.e., the normal vectors of the sub-region surfaces are parallel to one another; and different transducer elements may have the same or different numbers and/or shapes of the sub-regions. For example, referring to FIG. 6B, while the transducer element 632 is partitioned into four square sub-regions, the transducer element 634 may be partitioned into eight triangular sub-regions for further improving the steering ability in the diagonal direction. Additionally, the sub-regions in each transducer element or in different transducer elements may have the same or different shape. As used herein, a transducer element refers to one or more piezoelectric members that form a contiguous surface for transmitting the ultrasound waves/pulse; by "contiguous" is meant that the piezoelectric members are spatially in contact with one another and there is no physical border or barrier therebetween.

Figure 7A:
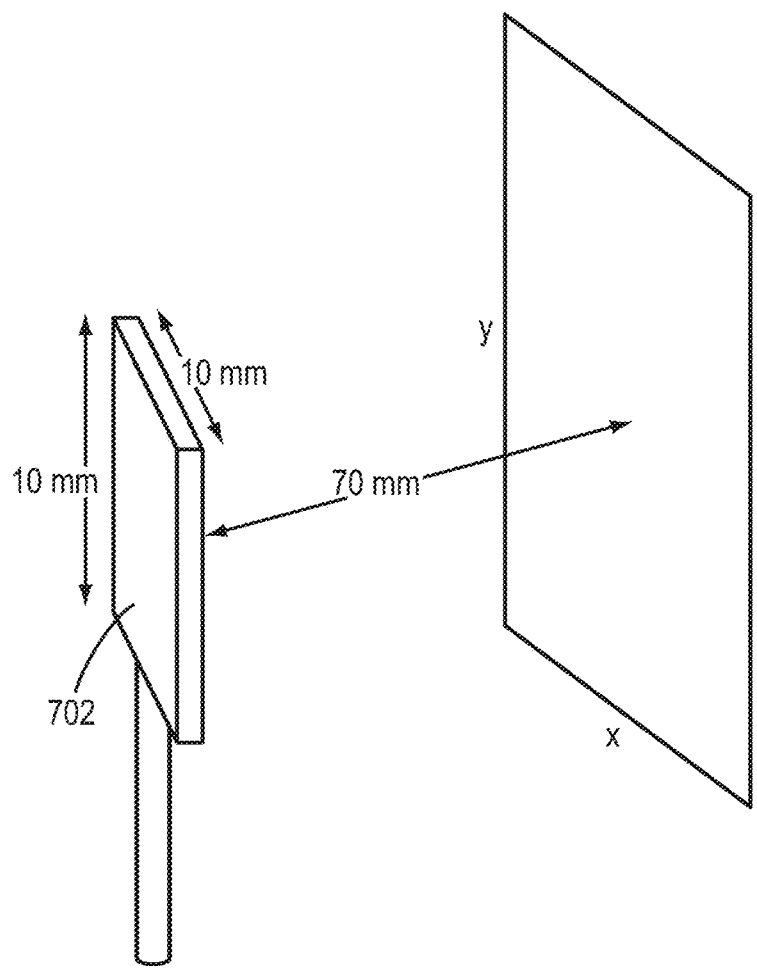
Figure 7B:
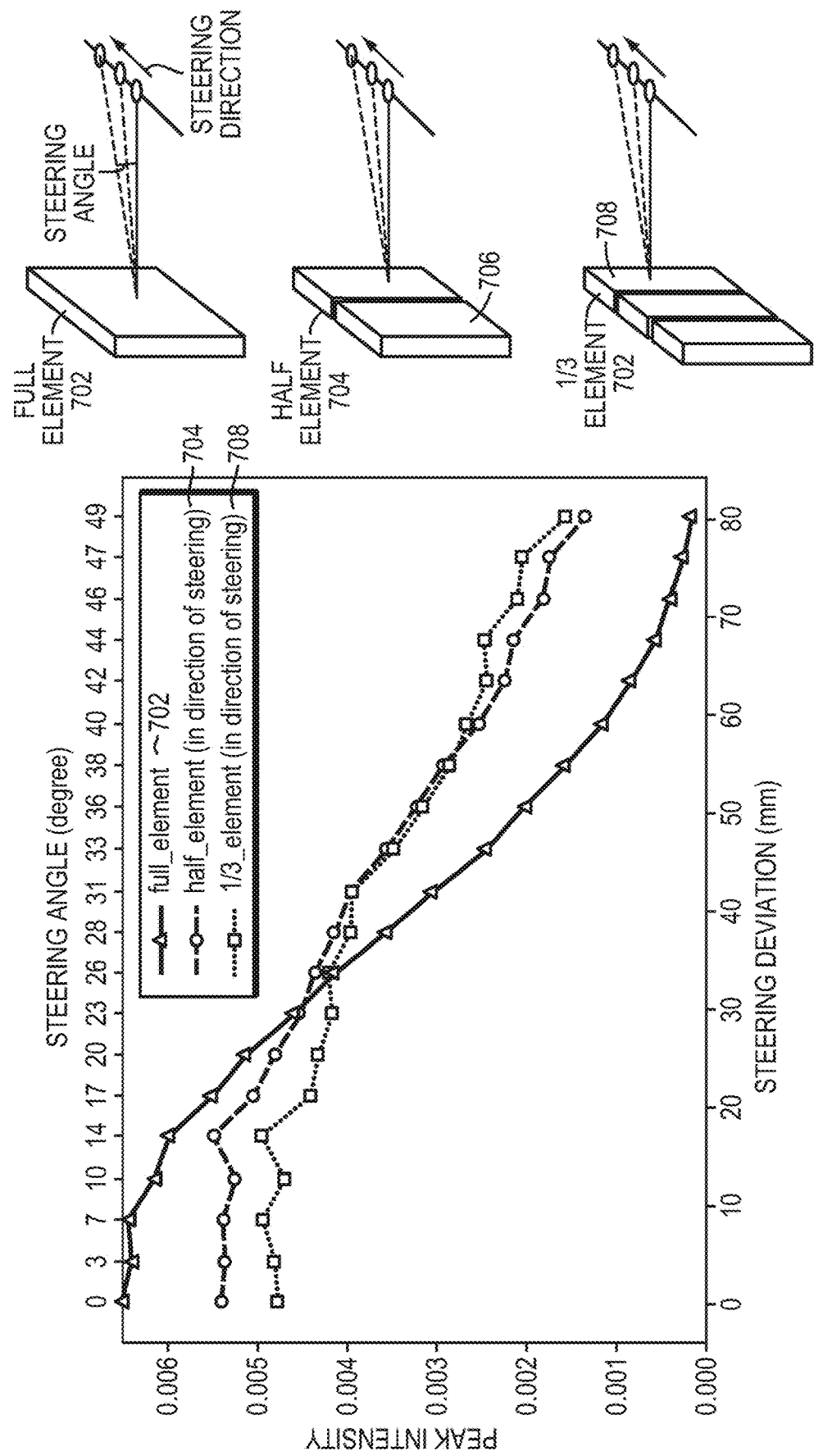

Prior to commencing the ultrasound treatment, the treatment planner may optionally predict the transducer element configuration that generates the maximal peak intensity or acoustic power at the target region based on, for example, the determined optimal frequency and the steering angle of the focal zone. For example, referring to FIGS. 7A and 7B, in an exemplary setup that a transducer element 702 has dimensions of 10×10 $mm^2$ and is 70 mm away from the focal plane, the peak intensity of the focal zone may depend on the steering angle α. FIG. 7B depicts how a prediction based on the physical model described above indicates that the maximal peak intensity occurs when the steering angle α=0°; the peak intensity then gradually decreases as the steering angle increases. In addition, when the steering angle α is below 25°, activation of the full element 702 may generate a higher peak intensity at the focal zone than other configurations; but activation of a half portion of the element in the direction of beam steering (i.e., the sub-region 704) may generate a higher peak intensity compared to activation of the full element 702 when the steering angle α exceeds 25°. Accordingly, based on the prediction, the ultrasound controller may be configured to activate the sub-regions of the transducer elements for generating the maximal peak intensity at a specific steering angle.

Figure 7C:
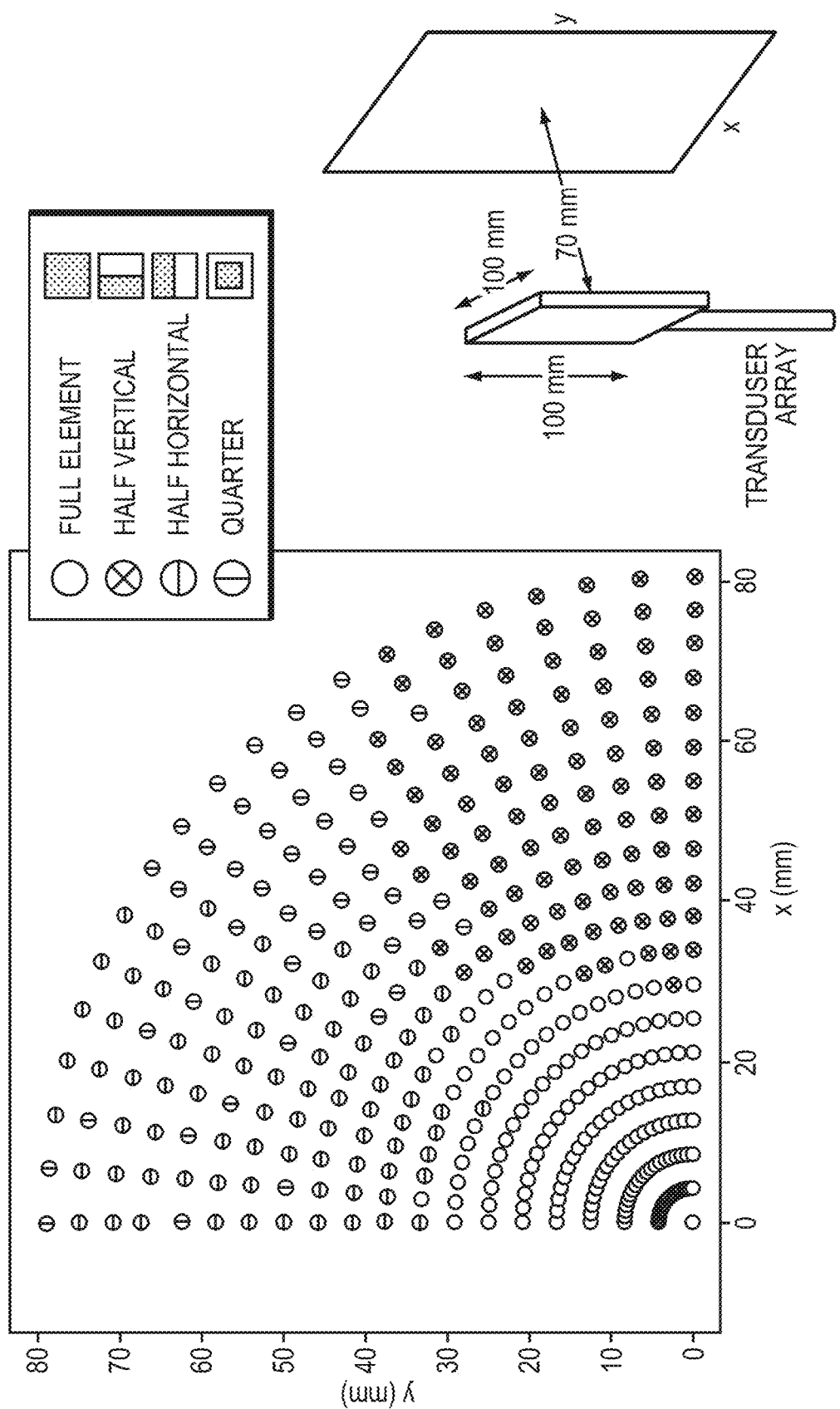
Figure 7D:
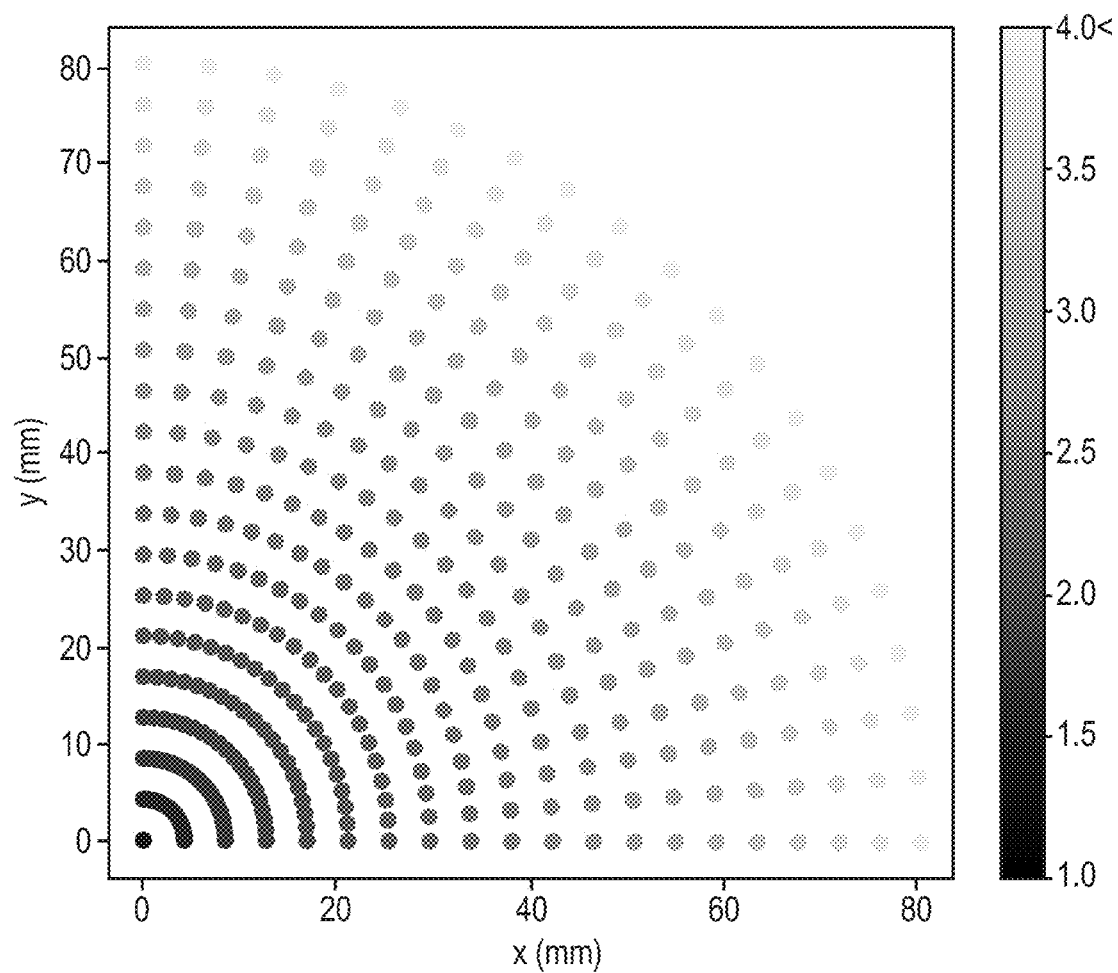

FIG. 7C depicts configurations of the transducer elements in a transducer array having dimensions of 100×100 mm² for generating maximal peak intensities at various locations on the focal plane. As shown, activation of the full elements is preferred when the steering angles are small. As the steering angle along the horizontal direction (i.e., x axis) increases; it may be preferable to activate half portions 704 of the elements in the steering direction (while deactivating the other half portions 706 of the elements) so as to maximize the peak intensity at the focal zone. Similarly, only half portions 710 of the elements in the horizontal direction may be activated to maximize the peak intensity when the beam is steered along the vertical direction (i.e., y axis); and quarter portions 712 of the elements may be activated to maximize the peak intensity along the diagonal steering direction. FIG. 7D depicts an improvement factor of the peak intensities at the focal zones generated by the transducer configurations in FIG. 7C compared with the peak intensities generated by the full elements of the transducer array. As shown, the improvement factor increases as the steering angle increases.

In various embodiments, the transducer elements may be configured to improve the peak intensity at a designated steering angle (or a range of steering angles). For example, referring to FIG. 7E, the ultrasound controller may be configured to activate the entire half portion 704 of the transducer elements on the steering side but only a half portion 716 of the half transducer elements 706 on the non-steering side while keeping the portion 718 deactivated; this may effectively improve the peak intensity for beam steering at the "midrange" steering angle (e.g., 15°<α<35°).

Accordingly, various embodiments further improve the peak intensity of the focal zone by adjusting the configurations of the transducer elements. This approach is particularly advantageous over the conventional ultrasound system 100 where the transducer elements are tiled to form a flat or curved surface, and once manufactured, neither the shape nor the size of individual transducer elements for activation can be changed. In addition, because various embodiments effectively allow the size of smallest controllable elements to be reduced and the number of the smallest controllable elements to be increased (i.e., by dividing the individual elements into multiple independently controllable sub-regions), the steering ability of the acoustic beam and the resolution thereof may be significantly improved.

Figure 1:
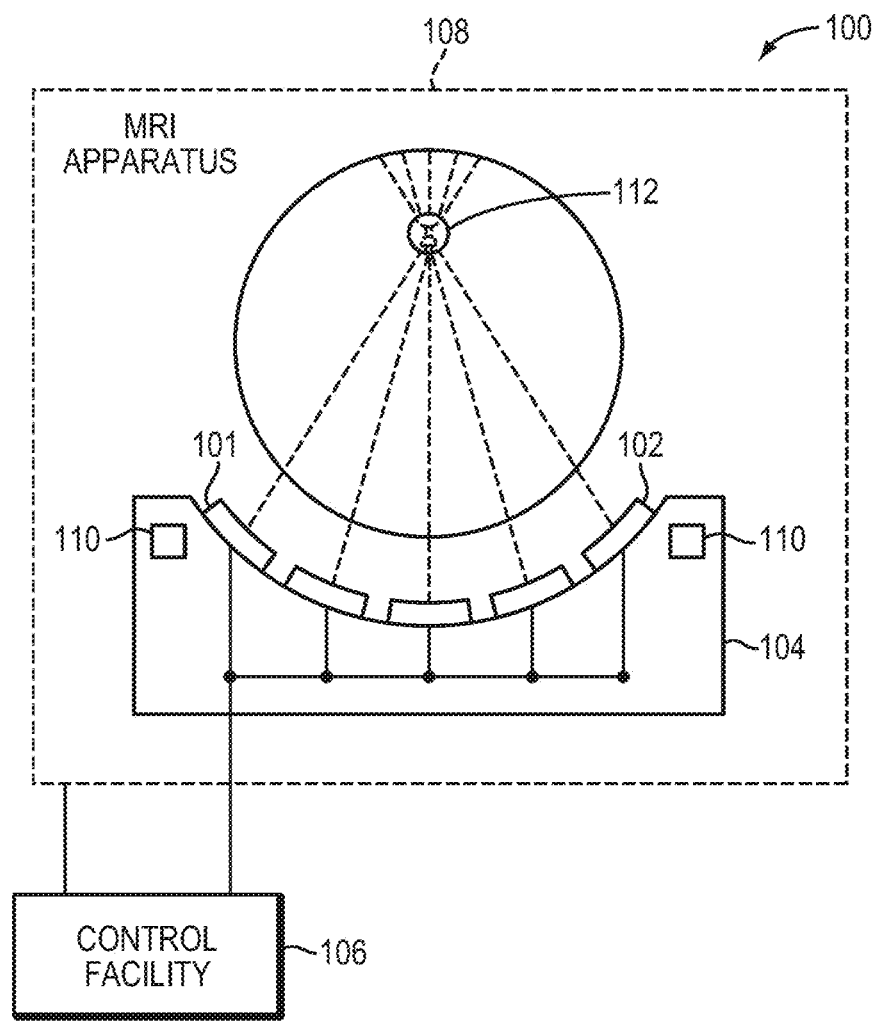
FIG. 1 schematically illustrates an exemplary focused ultrasound system in accordance with various embodiments.

The treatment planner utilized in the treatment-planning approach described above can be implemented in any suitable combination of hardware, software, firmware, or hardwiring in conjunction with one or more ultrasound transducers and imaging apparatus (e.g., an MRI apparatus) for measuring the peak intensity/power at the focus, or another parameter indicative thereof. The combination of hardware, software, firmware, or hardwiring may be integrated with the ultrasound controller (e.g., controller 106 of FIG. 1) and/or the imaging apparatus or other device for measuring peak acoustic intensity/power at the target (e.g., image-processing system 216 of FIG. 2), or provided as a separate device in communication therewith.

Figure 8:
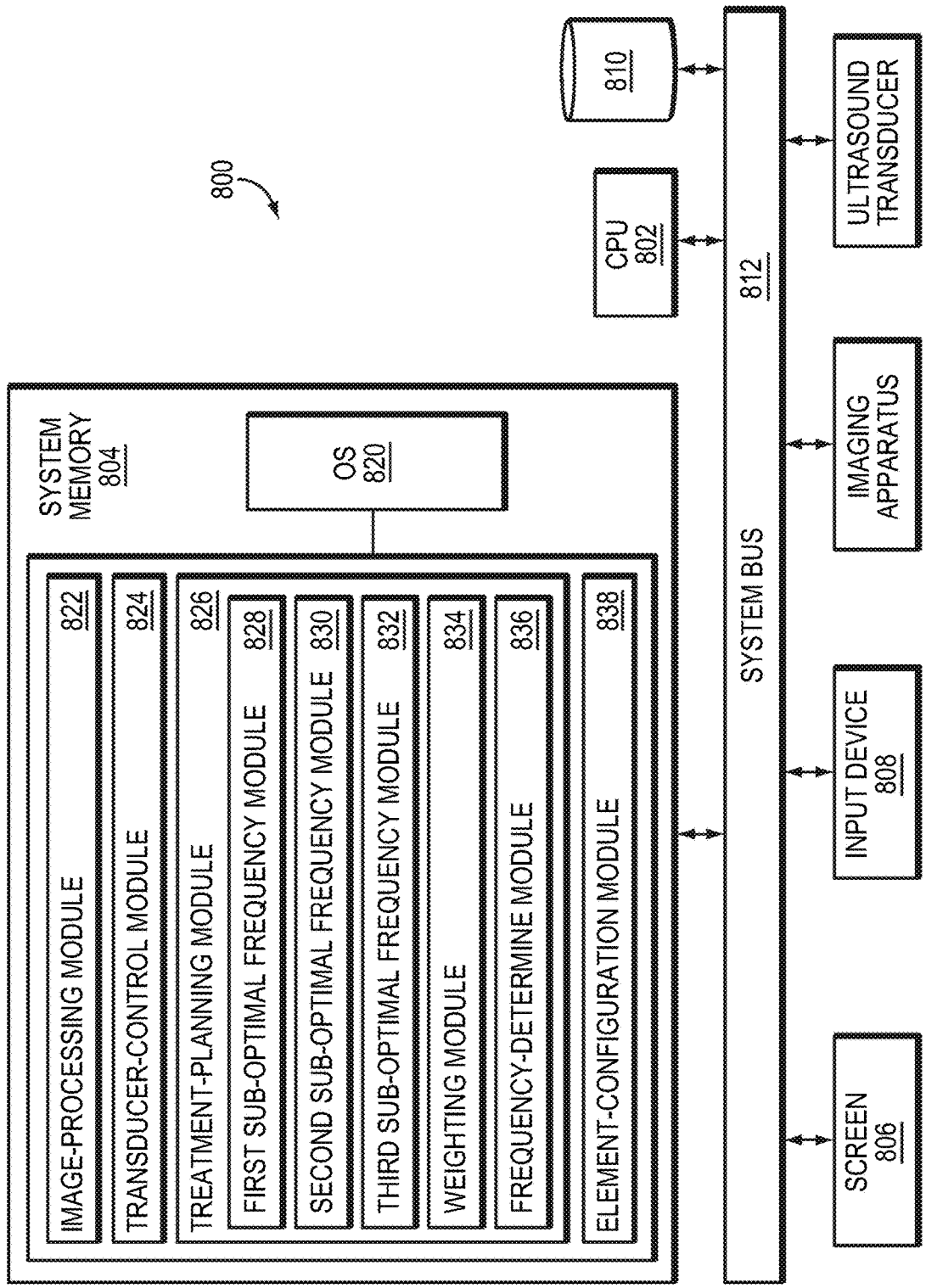
FIG. 8 is a block diagram illustrating a system for maximizing the peak intensity/power of a focused beam at the target region in accordance with various embodiments.

In some embodiments, the controller is implemented with a suitably programmed general-purpose computer; FIG. 8 shows an exemplary embodiment. The computer 800 includes one or more processors 802 (e.g., a CPU) and associated system memory 804 (e.g., RAM, ROM, and/or flash memory), user input/output devices (such as a screen 806 and a keyboard, mouse, etc. 808), and typically one or more (typically non-volatile) storage media 810 (e.g., a hard disk, CCD, DVD, USB memory key, etc.) and associates drives. The various components may communicate with each other and with external devices (such as the ultrasound transducer and/or the imaging apparatus) via one or more system buses 812.

The system memory 804 contains instructions, conceptually illustrated as a group of modules, that control the operation of the processor 802 and its interaction with the other hardware components. An operating system 820 directs the execution of low-level, basic system functions such as memory allocation, file management and operation of the peripheral devices. At a higher level, one or more service applications provide the computational functionality required for the treatment planner to determine the optimal frequency in accordance herewith. For example, as illustrated, the system may include an image-processing module 822 that allows analyzing images from the MRI (or other imaging) apparatus to identify the target therein and visualize the focus to ensure that it coincides with the target; a transducer-control module 824 for computing the relative phases and amplitudes of the transducer elements based on the target location as well as for controlling ultrasound-transducer operation during both frequency optimization and treatment; and a treatment-planning module 826 providing the computational functionality required for frequency optimization (e.g., acquiring data about the frequency-dependence of the peak acoustic intensity or power at the target and selecting an optimum frequency (or multiple respective optimum frequencies for various transducer segments) based thereon) in accordance with the approaches described in FIGS. 3, 4, 5D and 5E. More specifically, a first sub-module 828 may determine the first sub-optimal frequency corresponding to maximal energy absorption at the target; a second sub-module 830 may determine the second sub-optimal frequency $f_j$ corresponding to minimal energy attenuation of the focused beam propagating through the intervening tissue before reaching the target; a third sub-module 832 may determine one or more sub-optimal frequencies corresponding to other parameters affecting the peak acoustic intensity/power; a weighting module 834 may assign the weighting factors to the various sub-optimal frequencies in the manner described in detail above; and a frequency-determine module 836 for determining the optimal frequency based on the sub-optimal frequencies. The treatment-planning module 826 may be in communication with the image-processing module 822 to acquire information of the target/non-target regions obtained from the images and/or the transducer-control module 824 for providing the determined optimal frequency thereto so as to operate the transducer in accordance therewith. In addition, the system may include an element-configuration module 838 for determining the configurations (e.g., sizes and/or shapes) of the transducer elements at a specific steering angle for improved acoustic intensity/power; the transducer-control module 824 may then be responsive to the element-configuration module 838 and/or the treatment-planning module 826 for cause the transducer to sonicate the target in accordance with the determined configurations and optimal frequency.

Of course, the depicted organization of the computational functionality into various modules is but one possible way to group software functions; as a person of skill in the art will readily appreciate, fewer, more, or different modules may be used to facilitate frequency-optimization in accordance herewith. However grouped and organized, software may be programmed in any of a variety of suitable programming languages, including, without limitation, PYTHON, FORTRAN, PASCAL, JAVA, C, C++, C #, BASIC or combinations thereof. Furthermore, as an alternative to software instructions executed by a general-purpose processor, some or all of the functionality may be provided with programmable or hard-wired custom circuitry, including, e.g., a digital signal processor, programmable gate array, application-specific integrated circuit, etc.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. For example, instead of MR-based thermometry or ARFI, any non-invasive imaging technique capable of measuring the (physical or therapeutic) effect of the acoustic beam at the focus may generally be used to select an optimal frequency (or multiple optimal frequencies for different segments) in accordance herewith. Accordingly, the described embodiments are to be considered in all respects as only illustrative and not restrictive.

What is claimed is:

1. A system for delivering ultrasound energy to a target region, the system comprising:
    an ultrasound transducer comprising a plurality of transducer elements for generating a focal zone of acoustic energy at the target region, wherein each of the plurality of transducer elements is partitioned into a plurality of contiguous sub-regions having a common directionality;
    at least one driver circuit connected to the plurality of transducer elements;
    a switch matrix comprising a plurality of switches for switchably connecting the plurality of sub-regions of each of the plurality of transducer elements to the driver circuit, each of the plurality of sub-regions being associated with one of the plurality of switches; and
    a controller configured to:
        (a) determine an optimal sonication frequency for maximizing a peak acoustic intensity in the focal zone; and
        (b) for each of the plurality of transducer elements and based at least in part on the determined optimal sonication frequency, activate at least one but fewer than all of the plurality of switches in the switch matrix to thereby cause a corresponding sub-region of a corresponding transducer element to transmit ultrasound pulses to the target region at a steering angle greater than 25°, the ultrasound pulses having peak intensities higher than generated by activation of an entirety of the corresponding transducer element.

2. The system of claim 1, further comprising an imaging system for acquiring images of the target region or a non-target region located between the transducer and the target region.

3. The system of claim 2, wherein the imaging system comprises at least one of a computer tomography (CT) device, a magnetic resonance imaging device (MM), a positron emission tomography (PET) device, a single-photon emission computed tomography (SPECT) device, or an ultrasonography device.

4. The system of claim 2, wherein the controller is further configured to determine, based at least in part on the acquired images, a spatial configuration of the target region with respect to the transducer.

5. The system of claim 4, wherein the spatial configuration comprises at least one of an orientation or a location.

6. The system of claim 4, wherein the controller is further configured to compute a steering angle of the focal zone based at least in part on the spatial configuration of the target region with respect to the transducer.

7. The system of claim 6, wherein the controller is further configured to activate the at least one of the plurality of switches based at least in part on the computed steering angle.

8. The system of claim 2, wherein the controller is further configured to:
    determine a risk level associated with the non-target region based at least in part on the acquired images; and
    determine the optimal sonication frequency based at least in part on the risk level.

9. The system of claim 2, wherein the controller is further configured to:
    use a physical model to predict a thermal map of the target region and the non-target region based at least in part on the acquired images; and
    determine the optimal sonication frequency based at least in part on the predicted thermal map.

10. The system of claim 1, wherein the controller is further configured to:
    determine a plurality of sub-optimal frequencies, each associated with a parameter, wherein (i) a change in the parameter results in a change in the peak acoustic intensity in the focal zone and (ii) each of the plurality of sub-optimal frequencies corresponds to a maximum of the peak acoustic intensity resulting from changes in an associated parameter; and
    determine the optimal sonication frequency based at least in part on the plurality of sub-optimal frequencies.

11. The system of claim 10, wherein the controller is further configured to assign a weighting factor to each of the plurality of sub-optimal frequencies and determine the optimal sonication frequency based at least in part on the weighting factors.

12. The system of claim 11, wherein the controller is further configured to assign the weighting factors based on at least one of a first anatomic characteristic of the target region, a second anatomic characteristic of a non-target region located between the transducer and the target region, a steering angle of the focal zone, a contribution of each parameter to the maximum of the peak acoustic intensity, or retrospective data based on a study of patients who have undergone ultrasound treatment.

13. The system of claim 12, wherein the first or the second anatomic characteristic comprises at least one of a tissue type, a tissue property, a tissue structure, a tissue thickness, or a tissue density.

14. The system of claim 11, wherein the controller is further configured to assign the weighting factors using a machine-learning or evolutionary approach.

15. The system of claim 10, wherein the controller is further configured to determine a second one of the sub-optimal frequencies based at least in part on a first one of the sub-optimal frequencies.

16. The system of claim 1, wherein the controller is further configured to:
compute a resonance frequency of a microbubble in the target region; and
determine the optimal sonication frequency based at least in part on the resonance frequency of the microbubble.

17. The system of claim 1, wherein at least one of the plurality of switches is a micro-electromechanical system (MEMS) switch or a complementary metal-oxide-semiconductor (CMOS) switch.

18. A system for delivering ultrasound energy to a target region, the system comprising:
an ultrasound transducer comprising a plurality of transducer elements for generating a focal zone of acoustic energy at the target region, wherein each of the plurality of transducer elements is partitioned into a plurality of contiguous sub-regions having a common directionality;
at least one driver circuit connected to the plurality of transducer elements;
a switch matrix comprising a plurality of switches for switchably connecting the plurality of sub-regions of each of the plurality of transducer elements to the driver circuit, each of the plurality of sub-regions being associated with one of the plurality of switches;
at least one imaging system for measuring a spatial configuration of the target region with respect to the transducer; and
a controller configured to, for each of the plurality of transducer elements and based at least in part on the measured spatial configuration, activate at least one but fewer than all of the plurality of switches in the switch matrix to thereby cause a corresponding sub-region of a corresponding transducer element to transmit ultrasound pulses to the target region at a steering angle greater than 25°, the ultrasound pulses having peak intensities higher than generated by activation of an entirety of the corresponding transducer element.

19. The system of claim 18, wherein the controller is further configured to compute a steering angle of the focal zone based at least in part on the spatial configuration and activate the at least one of the plurality of switches based on the steering angle.

20. The system of claim 18, wherein the imaging system comprises at least one of a computer tomography (CT) device, a magnetic resonance imaging device, a positron emission tomography (PET) device, a single-photon emission computed tomography (SPECT) device, or an ultrasonography device.

21. The system of claim 18, wherein the spatial configuration comprises at least one of an orientation or a location.

22. The system of claim 18, wherein at least one of the plurality of switches is a micro-electromechanical system (MEMS) switch or a complementary metal-oxide-semiconductor (CMOS) switch.

23. A system for delivering ultrasound energy to a target region, the system comprising:
an ultrasound transducer comprising a plurality of transducer elements for generating a focal zone of acoustic energy at the target region, wherein (i) at least one of the plurality of transducer elements is partitioned into a plurality of contiguous sub-regions having a common directionality and (ii) a number, shape, and directionality of subregions of a first of the plurality of transducer elements is different from a number, shape, and directionality of subregions of another of the plurality of transducer elements;
at least one driver circuit connected to at least one of the plurality of transducer elements;
a switch matrix comprising a plurality of switches for switchably connecting the plurality of sub-regions of the at least one of the plurality of transducer elements to the driver circuit, each of the plurality of sub-regions being associated with one of the plurality of switches; and
a controller configured to:
(a) determine an optimal sonication frequency for maximizing a peak acoustic intensity in the focal zone; and
(b) based at least in part on the determined optimal sonication frequency, activate at least one but fewer than all of the plurality of switches in the switch matrix to thereby cause a corresponding sub-region of a corresponding transducer element to transmit ultrasound pulses to the target region at a steering angle greater than 25°, the ultrasound pulses having peak intensities higher than generated by activation of an entirety of the corresponding transducer element.

24. A system for delivering ultrasound energy to a target region, the system comprising:
an ultrasound transducer comprising a plurality of transducer elements for generating a focal zone of acoustic energy at the target region, wherein (i) at least one of the plurality of transducer elements is partitioned into a plurality of contiguous sub-regions having a common directionality and (ii) a number, shape, and directionality of subregions of a first of the plurality of transducer elements is different from a number, shape, and directionality of subregions of another of the plurality of transducer elements;
at least one driver circuit connected to at least one of the plurality of transducer elements;
a switch matrix comprising a plurality of switches for switchably connecting the plurality of sub-regions of the at least one of the plurality of transducer elements to the driver circuit, each of the plurality of sub-regions being associated with one of the plurality of switches;
at least one imaging system for measuring a spatial configuration of the target region with respect to the transducer; and
a controller configured to, based at least in part on the measured spatial configuration, activate at least one but fewer than all of the plurality of switches in the switch matrix to thereby cause a corresponding sub-region of a corresponding transducer element to transmit ultrasound pulses to the target region at a steering angle greater than 25°, the ultrasound pulses having peak intensities higher than generated by activation of an entirety of the corresponding transducer element.

* * * * *